United States Patent
Kelso et al.

(10) Patent No.: US 8,304,188 B2
(45) Date of Patent: *Nov. 6, 2012

(54) BARRIERS FOR FACILITATING BIOLOGICAL REACTIONS

(75) Inventors: David M. Kelso, Wilmette, IL (US); Kunal Sur, Evanston, IL (US); Zaheer Parpia, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/162,524

(22) Filed: Jun. 16, 2011

(65) Prior Publication Data

US 2011/0269190 A1 Nov. 3, 2011

Related U.S. Application Data

(63) Continuation of application No. 12/395,020, filed on Feb. 27, 2009, now Pat. No. 8,187,808.

(60) Provisional application No. 61/032,655, filed on Feb. 29, 2008.

(51) Int. Cl.
  *C12Q 1/68* (2006.01)
  *C12M 1/00* (2006.01)
  *G01N 15/06* (2006.01)
  *C07H 21/04* (2006.01)

(52) U.S. Cl. ............... 435/6.1; 435/91.1; 435/283.1; 435/288.4; 422/68.1; 422/527; 536/23.1

(58) Field of Classification Search .............. None
See application file for complete search history.

(56) References Cited

U.S. PATENT DOCUMENTS

| | | | |
|---|---|---|---|
| 4,921,612 A | 5/1990 | Sirkar | |
| 5,279,936 A * | 1/1994 | Vorpahl | 435/6.16 |
| 5,466,575 A | 11/1995 | Cozzette et al. | |
| 6,989,237 B2 | 1/2006 | Fulwyler et al. | |
| 7,745,129 B1 * | 6/2010 | Schatz | 435/6.1 |
| 2001/0029810 A1 | 10/2001 | Ho | |
| 2005/0191759 A1 | 9/2005 | Pedersen-Bjergaard et al. | |
| 2005/0202504 A1 | 9/2005 | Anderson et al. | |
| 2006/0134793 A1 | 6/2006 | Key | |
| 2007/0184463 A1 | 8/2007 | Molho et al. | |
| 2008/0226500 A1 | 9/2008 | Shikida et al. | |
| 2008/0254467 A1 | 10/2008 | Regan | |
| 2008/0277348 A1 | 11/2008 | Izumizawa | |
| 2009/0289213 A1 | 11/2009 | Pipper et al. | |

(Continued)

FOREIGN PATENT DOCUMENTS

KR   1020020021810 A   3/2002

(Continued)

OTHER PUBLICATIONS

Chin et al., "Communication to the editor on protein solubility in organic solvents", Biotechnology and Bioengineering vol. 44, pp. 140 (1994).

(Continued)

*Primary Examiner* — Betty Forman
(74) *Attorney, Agent, or Firm* — Judy M. Mohr; McDermott Will & Emery

(57) ABSTRACT

The present invention relates to systems, devices, and methods for performing biological reactions. In particular, the present invention relates to the use of lipophilic, water immiscible, or hydrophobic barriers in sample separation, purification, modification, and analysis processes.

21 Claims, 21 Drawing Sheets

U.S. PATENT DOCUMENTS

2010/0291666 A1    11/2010    Collier et al.

FOREIGN PATENT DOCUMENTS

WO    WO 2005/069015 A1    7/2005
WO    WO 2006/071770 A2    7/2006

OTHER PUBLICATIONS

Dineva et al, "Sample preparation: a challenge in the development of point-of-care nucleic acid based assays for resource-limited settings", Analyst, vol. 132, pp. 1193-1199 (2007).

Furlani and Ng, "Analytical model of magnetic nanoparticle transport and capture in the microvasculature", Physical Review E73, 061919-1-061919-10.

Liu et al, "Self-contained, fully integrated biochip for sample preparation, polymerase chain reaction amplification and DNA microarray detection", Analytical Chemistry, vol. 76, pp. 1824-1831 (2004).

Mylonakis et al., "Plasma viral load testing in the management of HIV infection", Am. Fam. Physician vol. 63, No. 3, pp. 483 (2001).

Pipper et al., "Catching bird flu in a droplet", Nature Medicine, vol. 13, No. 10, pp. 1259-1263 and supplementary information, Fig. 1-5, pp. 1-5 (2007).

Shikida et al, "Development of an enzymatic reaction device using magnetic bead-cluster handling", J. Micromech. Microeng., vol. 16, pp. 1875-1883 (2006).

* cited by examiner

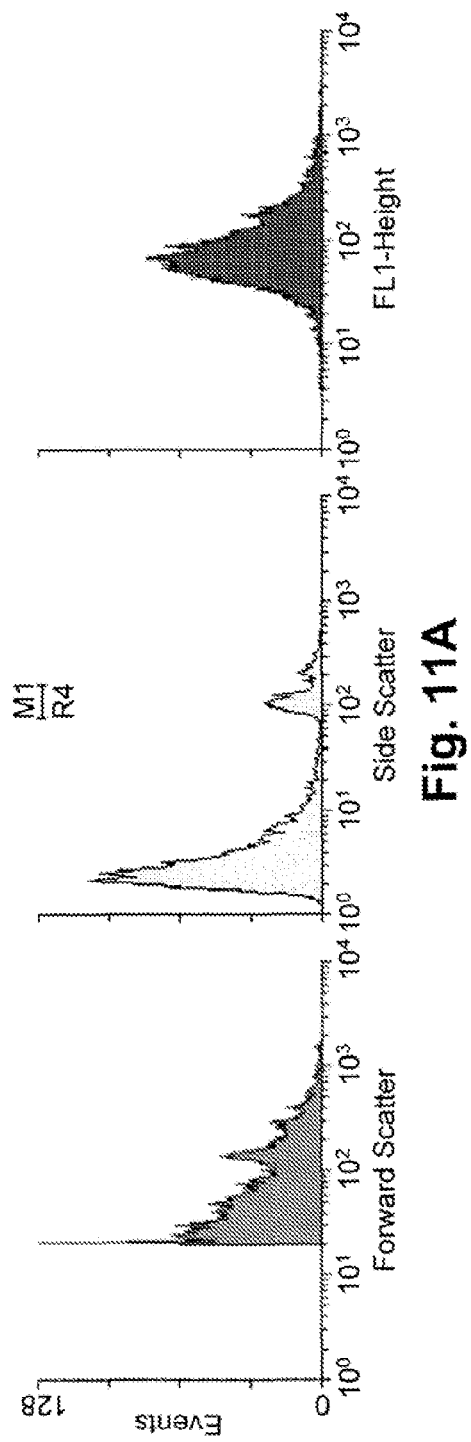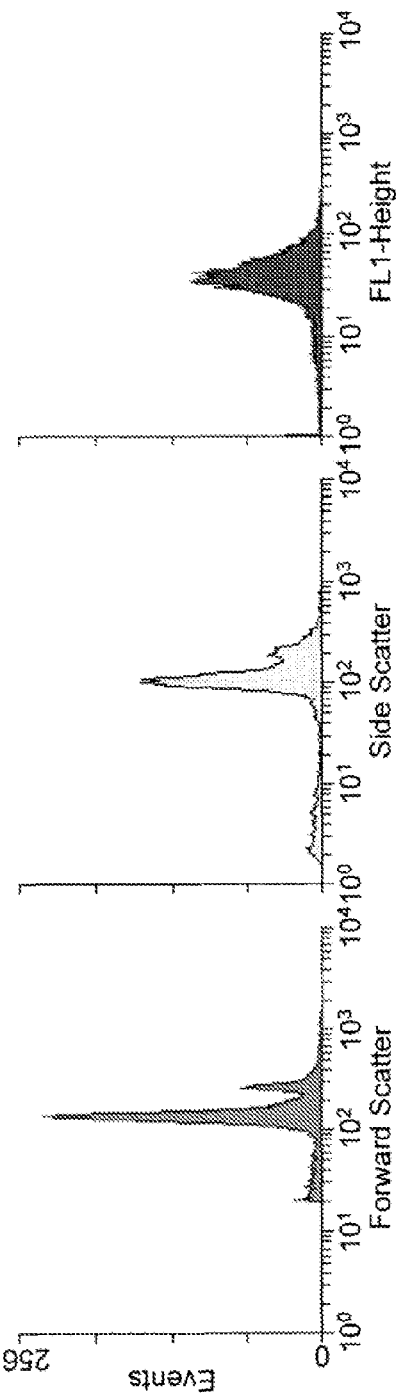

BARRIERS FOR FACILITATING BIOLOGICAL REACTIONS

CROSS REFERENCE TO RELATED APPLICATIONS

This application is a continuation of U.S. application Ser. No. 12/395,020 filed Feb. 27, 2009, which claims priority to U.S. Provisional Patent Application Ser. No. 61/032,655, filed Feb. 29, 2008, which is herein incorporated by reference in its entirety.

GOVERNMENT SUPPORT

This invention was made with government support under Grant No. CCF0329957 awarded by the National Science Foundation and Grant No. 5R01 EB001418-03 awarded by the National Institutes of Health. The government has certain rights in the invention.

FIELD OF THE INVENTION

The present invention relates to systems, devices, and methods for performing biological reactions. In particular, the present invention relates to the use of hydrophobic, water-immiscible, or lipophilic barriers in sample separation, purification, modification, and analysis processes.

BACKGROUND OF THE INVENTION

There is a great need for cost-effective, easy to use systems, methods, and devices for analyzing biological samples. Many commercially available systems cost tens to hundreds of thousands of dollars and have many moving parts which make them prone to failure. Because of the cost and complexity of such systems, their use has generally been limited to clinical laboratories which have the personnel and services needed to support their operation and maintenance.

One class of fully integrated automated analyzers, represented by the Abbott Architect, Siemens Centaur, Roche Elecsys, and others, perform immunoassays. Another class of modular analyzers, represented by the Abbott m2000, Roche COBAS, bioMérieux NucliSENS and others, perform nucleic acid assays. Much of the complexity of these systems is a result of separation steps involved in processing the assays.

Modular systems are also frequently used in research laboratories. Immunoassay separations may be performed by plate washers such as Titertek MAP-C2, BioTek ELx50, Tecan PW 96/384 and others. Nucleic acid separations are performed by systems such as the Applied Biosystems PRISM™ 6100, Invitrogen iPrep, Thermo Scientific KingFisher, Promega Maxwell, and others.

The availability of low-cost, reliable analyzers is of particular concern as it relates to the diagnosis and management of disease around the world. This problem is vividly illustrated by the problems associated with management of HIV infections. Many technologies exist that permit detection of nucleic acids or protein levels associated with HIV. This detection is important for managing the patient care of those infected by HIV. However, the cost and complexity of these systems prohibits their widespread use.

SUMMARY OF THE INVENTION

The present invention relates to systems, devices, and methods for performing biological reactions. In particular, the present invention relates to the use of hydrophobic, water or alcohol-immiscible, or lipophilic barriers in sample separation, purification, modification, and analysis processes.

In some embodiments, the present invention provides a biological sample purification end/or analysis device, comprising: a plurality of sample processing chambers comprising reagents for biological molecule or cell purification, modification analysis, and/or detection; and a lipophilic substance in between (e.g., separating) two or more of the chambers. In some embodiments, the lipophilic substance is a wax. In some embodiments, the wax is a phase change wax that can take liquid or solid form at pre-determined temperatures. For example, in some embodiments, the wax takes solid form at storing or shipping temperatures and liquid form at reaction temperature (e.g., room temperature). In some embodiments, the lipophilic substance is an oil. In some embodiments, there are two reaction chambers. In some embodiments, there are three reaction chambers. In some embodiments, there are four reaction chambers in some embodiments, there are five reactions chambers. In some embodiments, there are six or more reaction chambers (e.g., 7, 8, 9, 10, 11, . . . , 20, . . . ). In some embodiments, the lipophilic material provides a contiguous barrier between two or more of the chambers (i.e., a sample passes from a first chamber directly into the lipophilic material and directly out of the lipophilic material into the second chamber). In other embodiments, there is air, liquid, or other material between the lipophilic material and one or more of the chambers. In such embodiments, the lipophilic material is positioned such that a sample or biological molecule to be processed passes through the lipophilic material at some point between its transit from a first chamber to a second chamber.

In some embodiments, all of, or a subset of the reaction chambers are dedicated for sample purification. For example, one or more reaction chambers contain reagents that cause a sample purification event to occur, including, but not limited to, cell lysis, biological molecule capture, biological molecule separation, and cellular culture, purification, and/or analysis. In some embodiments, all of, or a subset of the reactions chambers are dedicated for sample modification. For example, one or more reaction chambers contain reagents that cause a biological molecule (e.g., nucleic acid, protein, lipid, etc.) or cell modification event to occur, including, but not limited to, amplification, ligation, cleavage, labeling, extension, degradation, association with a ligand, oligomerization, transfection, transformation, transgenesis, division, differentiation, and the like. In some embodiments, all of, or a subset of the reaction chambers are dedicated for sample analysis. For example, one or more reaction chambers contain reagents or other components that permit detection or other types of analysis of a biological molecule or cells of interest. In some embodiments, the chambers contain reagents that permit development of a color, fluorescent signal, luminescent signal or other detectable characteristic. In some embodiments, the chambers are configured to optimize signal detection by a signal reader (e.g., color reader, fluorescence reader, luminescence reader, the human eye, etc.). One or more of the chambers may be used for multiple different tasks, including purification, modification, analysis, and/or detection.

The present invention is not limited by the manner in which the chambers are configured or separated from one another. The chambers may each be the same size and shape as one another or may be different sizes or shapes. A wide variety of configurations may be used. In some embodiments, the chambers are wells and the lipophilic barrier sits on top of or below the wells, such that any material that is transferred from one chamber to another, must pass through the lipophilic material by moving up or down, and over. In some embodiments, the chambers are created by the existence of the lipophilic material. For example, in some embodiments, a lipophilic material is deposited along one or more points in a channel or channels (e.g., in a glass, plastic, or ceramic tube), to create barriers between zones in the channel or channels. The channel may be any size, including small sizes such as capillary tubes or microfluidic channels. In some embodiments, that chambers and barriers are configured so that a sample or biological molecule of interest must travel through a linear series of reaction chambers. However, in other embodiments, a sample or biological molecule in a first reaction chamber may optionally skip one or more other chambers. In some embodiments, the chambers are housed in a device that has a size or shape configured to fit existing laboratory equipment (e.g., automated robotic arms, plate holders (e.g., 96-well), thermocyclers, fluorescent detectors, etc.). In some embodiments, channels are used to separate reaction chambers, where all or a portion of the channel contains the lipophilic material. For example, in some embodiments, the device is configured similar to a 96-well or 384-well plate with channels connecting two more of the wells. In some embodiments, a pathway between two chambers contains air, water, or other fluids, where the sample passes through the air, water, or other fluid before and/or after entering or leaving the lipophilic material.

In some embodiments, reaction chambers are microwells or microtubes containing hydrophilic solutions and the lipophilic substance is placed on top of or below the solution in a subset of the chambers or in a separate chamber.

In some embodiments, the device comprises a transport mechanism that permits transfer of a desired material from one reaction chamber to another through the lipophilic material. For example, in some embodiments, a biological molecule of interest is associated with a magnetic particle, such as a magnetic bead, in one of the reaction chambers. The biological molecule of interest is moved from one chamber to the other by application of a magnetic field (e.g., from a magnet) that causes the magnetic particle to travel from a first chamber, through the lipophilic barrier, to a second chamber. In other embodiments, an electrical field is created to move biological molecules or components associated with the biological molecules (e.g., ligands, beads, charge tags, etc.), using charge, from one reaction chamber to another. In some embodiments, centrifugal force is used to move biological molecules of interest from one chamber to another, through the lipophilic barrier. In some embodiments, pressure from a vacuum or from suction is used to move materials between chambers. The present invention is not limited by the mechanism of transport.

In some embodiments, the device comprises a vapor barrier to prevent or reduce the loss of liquid during handling or use. In some embodiments, the device is composed of a plurality of thin layers of material stacked on one another. For example, in some embodiments, the layers comprise an aluminum foil layer sandwiched between plastic layers.

In some embodiments, the devices of the invention are provided as a system e.g., kit) that includes one or more other components that permit sample acquisition, sample handling, sample disposal, data collection, data analysis, and data presentation. These components may be separate devices or may be integrated into a single multi-component device. These components may include, but are not limited to, medical devices, environmental sample handling devices, protein purification devices, nucleic acid purification devices, computers, software, and the like. One or more components of the system or device can be automated. In some embodiments, one or more components of the system are configured to work without automation. For example, in a non-automated system, a handheld magnet is provided to move samples from one chamber to another, a heat block or water bath is used to create the desired reactions temperatures, a hand held fluorescence detector is used to detect signal or a signal is observed by eye.

The systems and devices of the invention find use with a wide variety of samples. For example, in some embodiments, a sample is a biological or environmental sample. Biological samples may be obtained from animals (including humans) and encompass fluids, solids, tissues, and gases. Biological samples include blood products, such as plasma, serum and the like, as well as cerebrospinal fluid, sputum, bronchial washing, bronchial aspirates, urine, lymph fluids, and various external secretions of the respiratory, intestinal and genitourinary tracts, tears, saliva, milk, white blood cells, myelomas, biological fluids such as cell culture supernatants, tissue (fixed or not fixed), cell (fixed or not fixed), and the like. Environmental samples include, but are not limited to, environmental material such as surface matter, soil, water, and industrial samples.

DESCRIPTION OF THE FIGURES

FIG. 11a shows the signal of streptavidin coated particles after moving through oil containing a fluorescent dye. FIG. 11b shows the signal of streptavidin coated particles after moving through oil containing a fluorescent dye followed by agitation of the particles in PBS buffer.

DEFINITIONS

Figure 1:
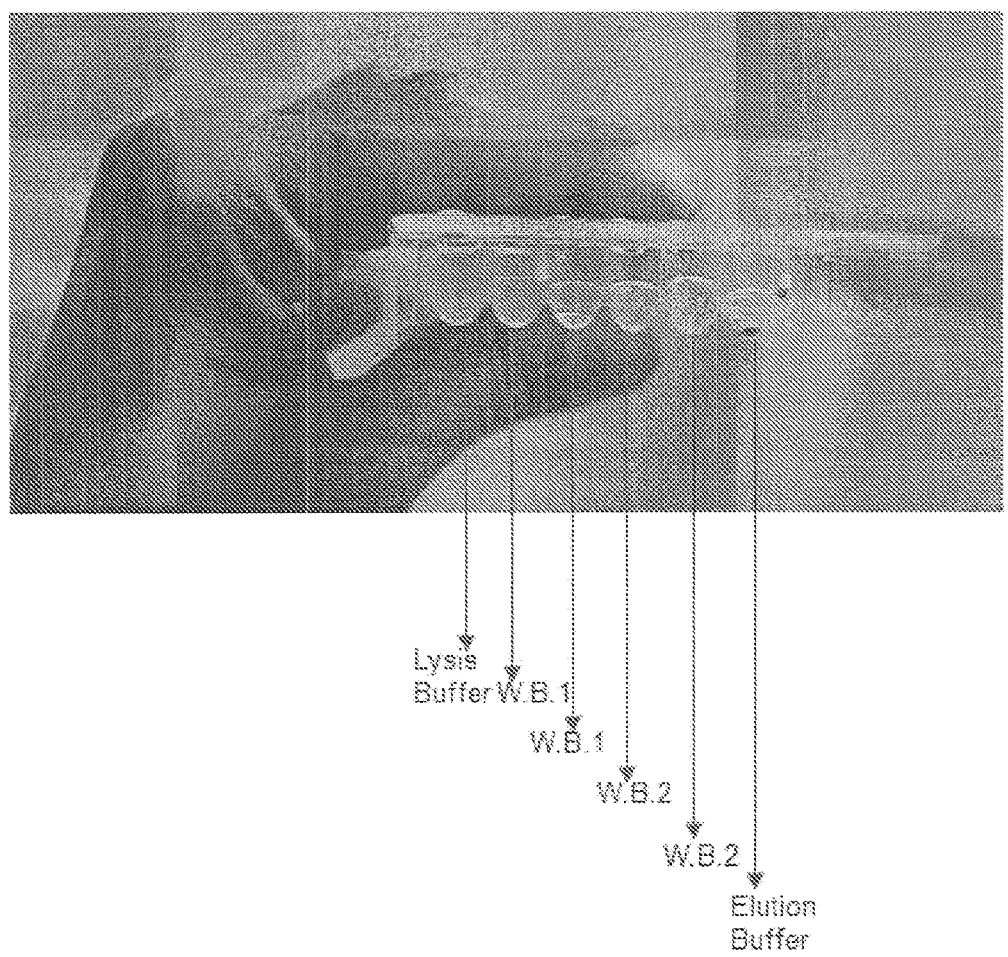
FIG. 1 shows a cartridge for sample purification and PCR in accord with some embodiments of the present invention.

To facilitate an understanding of this disclosure, terms are defined below:

As used herein, the term "lipophilic material" refers to any substance which is substantially immiscible in water, alcohol, or other hydrophilic or aqueous fluid. In some embodiments, lipophilic materials of the present invention have a low solubility for substances that interfere with a particular biological process such as nucleic amplification or biomolecule detection. In some embodiments, lipophilic materials of the invention have a low vapor pressure. Lipophilic substances tend to interact within themselves and with other substances through van der Waals forces. They have little to no capacity to form hydrogen bonds. Lipophilic substances typically have large o/w (oil/water) partition coefficients.

"Water insoluble" and "hydrophobic" materials are used synonymously in this specification. The terms include polymers that are practically insoluble in water and freely soluble in volatile lipophilic solvents such as methylene chloride and non-volatile hydrophilic solvents, particularly N-methylpyrollidone (NMP).

"Water-miscible" or "hydrophilic" materials refer to an organic liquid that can be diluted with at least an equal part of water without separation.

A property of "water-immiscible" or "lipophilic" materials is that they cannot be diluted with at least an equal part of water without separation.

"Purified polypeptide" or "purified protein" or "purified nucleic acid" means a polypeptide or nucleic acid of interest or fragment thereof which is essentially free of, e.g., contains less than about 50%, preferably less than about 70%, and more preferably less than about 90%, cellular components with which the polypeptide or polynucleotide of interest is naturally associated.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and include all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid of lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myrisoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as for instance Proteins—Structure and Molecular Properties, 2.sup.nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pg. 1-12 in Posttranslational Covalent Modification of Proteins, B. C. Johnson, Ed., Academic Press, New York (1983); Seifter et al., Analysis for protein modifications and nonprotein cofactors, Meth. Enzymol. 182: 626-646 (1990) and Rattan et al., Protein synthesis: Posttransiational Modifications and Aging, Ann N.Y. Acad. Sci. 663: 48-62 (1992).

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched, and branched circular polypeptides may be synthesized by non-translational natural process and by entirely synthetic methods as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to express efficiently mammalian proteins having native patterns of glycosylation. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

The term "mature" polypeptide refers to a polypeptide which has undergone a complete, post-translational modification appropriate for the subject polypeptide and the cell of origin.

A "fragment" of a specified polypeptide refers to an amino acid sequence which comprises at least about 3-5 amino acids, more preferably at least about 8-10 amino acids, and even more preferably at least about 15-20 amino acids derived from the specified polypeptide.

The term "immunologically identifiable with/as" refers to the presence of epitope(s) and polypeptide(s) which also are present in and are unique to the designated polypeptide(s). Immunological identity may be determined by antibody binding and/or competition in binding. The uniqueness of an epitope also can be determined by computer searches of known data banks, such as GenBank, for the polynucleotide sequence which encodes the epitope and by amino acid sequence comparisons with other known proteins.

As used herein, "epitope" means an antigenic determinant of a polypeptide or protein. Conceivably, an epitope can comprise three amino acids in a spatial conformation which is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

"Purified product" refers to a preparation of the product which has been isolated from the cellular constituents with which the product is normally associated and from other types of cells which may be present in the sample of interest.

"Analyte," as used herein, is the substance to be detected which may be present in the test sample, including, biological molecules of interest, small molecules, pathogens, and the like. The analyte can include a protein, a polypeptide, an amino acid, a nucleotide target and the like. The analyte can be soluble in a body fluid such as blood, blood plasma or serum, urine or the like. The analyte can be in a tissue, either on a cell surface or within a cell. The analyte can be on or in a cell dispersed in a body fluid such as blood, urine, breast aspirate, or obtained as a biopsy sample.

A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

Specific binding members include "specific binding molecules." A "specific binding molecule" intends any specific binding member, particularly an immunoreactive specific binding member. As such, the term "specific binding molecule" encompasses antibody molecules (obtained from both polyclonal and monoclonal preparations), as well as, the following: hybrid (chimeric) antibody molecules (see, for example, Winter, et al., Nature 349: 293-299 (1991), and U.S. Pat. No. 4,816,567); F(ab').sub.2 and F(ab) fragments; Fv molecules (non-covalent heterodimers, see, for example, Inbar, et al., Proc. Natl. Acad. Sci. USA 69: 2659-2662 (1972), and Ehrlich, et al., Biochem, 19: 4091-4096 (1980)); single chain Fv molecules (sFv) (see, for example, Huston, et al., Proc. Natl. Acad. Sci. USA 85: 5879-5883 (1988)); humanized antibody molecules (see, for example, Riechmann, et al., Nature 332: 323-327 (1988), Verhoeyan, et al., Science 239: 1534-1536 (1988), and UK Patent Publication No. GB 2,276,169, published 21 Sep. 1994); and, any functional fragments obtained from such molecules, wherein such fragments retain immunological binding properties of the parent antibody molecule.

The term "hapten," as used herein, refers to a partial antigen croon-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means. In some embodiments, the indicator reagent is conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodamine, chemiluminescent compounds such as dioxetanes, acridiniums, phenanthridiniums and lumina radioactive elements and direct visual labels. Examples of enzymes include alkaline phosphatase, horseradish peroxidase, beta-galactosidase and the like. The selection of a particular label is not critical, but it should be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips, are all suitable examples. It is contemplated and within the scope of the present invention that the solid phase also can comprise any suitable porous material.

As used herein, the terms "detect", "detecting", or "detection" may describe either the general act of discovering or discerning or the specific observation of a detectably labeled composition.

The term "polynucleotide" refers to a polymer of ribonucleic acid (RNA), deoxyribonucleic acid (DNA), modified RNA or DNA, or RNA or DNA mimetics. This term, therefore, includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 5-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3 ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "nucleic acid amplification reagents" includes conventional reagents employed in amplification reactions and includes, but is not limited to, one or more enzymes having polymerase activity, enzyme cofactors (such as magnesium or nicotinamide adenine dinucleotide (NAD)), salts, buffers, deoxynucleotide triphosphates (dNTPs; for example, deoxyadenosine triphosphate, deoxyguanosine triphosphate, deoxycytidine triphosphate and deoxythymidine triphosphate) and other reagents that modulate the activity of the polymerase enzyme or the specificity of the primers.

As used herein, the terms "complementary" or "complementarity" are used in reference to polynucleotides (i.e., a sequence of nucleotides such as an oligonucleotide or a target nucleic acid) related by the base-pairing rules. Complementarity may be "partial," in which only some of the nucleic acids' bases are matched according to the base pairing rules. Or, there may be "complete" or "total" complementarity between the nucleic acids. The degree of complementarily between nucleic acid strands has significant effects on the efficiency and strength of hybridization between nucleic acid strands. This is of particular importance in amplification reactions, as well as detection methods which depend upon binding between nucleic acids.

The term "homology" refers to a degree of identity. There may be partial homology or complete homology. A partially identical sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids.

As used herein, the term "Tm" is used in reference to the "melting temperature." The melting temperature is the temperature at which a population of double-stranded nucleic acid molecules becomes half dissociated into single strands. The equation for calculating the Tin of nucleic acids is well known in the art. As indicated by standard references, a simple estimate of the Tm value may be calculated by the equation: $Tm=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references include more sophisticated computations which take structural as well as sequence characteristics into account for the calculation of Tm.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably at least 5 nucleotides, more preferably at least about 10-15 nucleotides and more preferably at least about 15 to 30 nucleotides, or longer. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

DETAILED DESCRIPTION OF THE INVENTION

The present invention relates to systems, devices, and methods for performing biological reactions, in particular, the present invention relates to the use of lipophilic barriers in sample separation, purification, modification, and analysis processes.

The systems, devices, and methods of the invention may be configured, if desired, as inexpensive and easy-to-use sample purification and/or modification and/or analysis and/or detection systems. For example, embodiments of the present invention, described herein, provide an economical means for widespread biological molecule detection, analysis, and characterization. These systems, device, and methods find many uses. To illustrate aspect and benefits of the invention, its application to nucleic acid and protein analysis, particularly for monitoring HIV infection and status, are provided below. The invention is not limited to these illustrative embodiments. In some embodiments, the systems, devices, and methods of the invention are utilized in conjunction with existing, complex, expensive sample separation, purification, modification, and analysis equipments. For example, in some embodiments, the approaches of the present invention are used for sample preparation (e.g., nucleic acid or polypeptide purification) prior to modification and/or analysis using traditional equipment thermocyclers, mass spectrometers, NMR devices, etc.).

There are 35 million adults and children living with HIV/AIDS, 22 million of them in sub-Saharan Africa. The average clinic in Africa treats about 400 patients and the problem of transportation is leading to an increase in the number of clinics rather than the growth of large central facilities. Therefore, there is a need for more than 100,000 viral load measuring machines. The major limitations of currently available viral load assays include the cost of the required instruments, the complex and time-consuming procedures leading to the need for highly trained personnel, and the need for cold-chain shipment of reagents.

The development of affordable and simple HIV viral load assays is a critical step for improving the quality of AIDS patient care in the developing world. This would require automating complex diagnostic procedures that are normally performed in a centralized laboratory into small point of care (POC) devices; this capability could empower health-care workers and patients with important health-related information in even the most remote settings. The required HIV viral load assay should preferably deliver answers at the point of care, but moving it from remote central laboratories to district hospital labs closer to the patient will improve outcomes. Such a device will perform separation, amplification, and detection of HIV with a short turnaround time and at an affordable cost. A short time is critical since it would reduce the number of machines needed in a clinic and reduce the time spent by the patient at the clinic, thereby reducing the actual cost.

Many challenges must be overcome when conducting HIV viral load assays both in centralized laboratories and out in the field. Large laboratories use automated or semi-automated robotic systems for high-volume HIV viral load assays. However, sample processing is typically the most troublesome part of these tests. Currently, sample-processing procedures involve many steps, often requiring centrifugation and extraction steps. Also, these methods often do not adequately purify the target nucleic acid. They often leave inhibitory or interfering, substances in the reaction mixture that can cause inhibition of the amplification reaction and result in false-negative results. The manual nature of current sample-processing techniques also can lead to specimen cross-contamination, which can cause false-positive results.

Considerable effort has been made in trying to automate the sample preparation process, since this would allow for the more widespread use of PCR or other nucleic analysis techniques. However, existing automated high-throughput systems perform multiple extraction and purification steps, and still require certain manual preparations, including sample and reagent loading, and waste removal. Hence, highly trained technicians are required to conduct the assay and maintain the instrument. The automated systems are very expensive because they use complex robotic arms to move solutions or magnetic particles and precision instruments to pipette liquids. The cost of an automated system is often difficult to justify for smaller laboratories, especially those in resource limited settings. Cross-contamination is also a problem since they employ amplification technologies. Clinical laboratories often use separate rooms for reagent preparation, sample preparation, amplification, and post-amplification analysis. For these reasons, despite the automation, viral load testing is considered high-complexity tests under the Clinical Laboratory Improvement Amendments (CLIA), To date, no Nucleic Acid Test (NAT) system has qualified for CLIA-waived status, largely because of the difficulties in automating sample preparation and reagent handling.

Performing field-use or near-patient NATs involves even more challenges, especially since they will inevitably be conducted by less-experienced users in non-laboratory environments. The following systems have recently been developed for deployment of NATs in the field.

The GeneXpert system by Cepheid (Sunnyvale, Calif.) is one of the first PCR-based instruments that integrate sample preparation, amplification, and detection. The disposable single-test GeneXpert sample-preparation cartridge consists of four functional components: the cap, the cartridge body, the valve body assembly, and the micro volume PCR reaction tube. The cartridge body is divided internally into a number of chambers of various sizes and functions, some containing the lyophilized reagent beads, and each with a port at the bottom for fluidic inflow and outflow. The chambers are radially arranged around the syringe barrel in the center. The valve body assembly, located below the cartridge body, is the site of cell lysing and DNA purification, under software control, a rotary valve on the instrument moves the valve body assembly so that fluids can be aspirated from or dispensed into the appropriate chamber for mixing, dilution, and washing, according to the programmed assay protocol. The reaction tube, which projects from the cartridge, receives the prepared sample and interfaces with the PCR reactor for amplification and detection of the target analyte. To perform a test on the GeneXpert system, the operator opens the cartridge cap and loads the liquid sample into the sample chamber. When the operator closes the cap, the cartridge is permanently sealed throughout the testing procedure and biohazard disposal, eliminating any risk of cross-contamination of samples. Cells are lysed by agitating tiny glass beads in the valve body assembly by ultrasound generated directly below the cartridge. The extracted DNA flows into a micro fluidic channel containing immobilized DNA probes that DNA as the cellular debris flows over. The bound DNA is later released from its attachment site and washed off for PCR amplification.

Another system developed by IQuum Inc (Allston, Mass.) is the Liat Molecular Analyzer based on its proprietary lab-in-a-tube (Liat) technology platform. The Liat tube uses a flexible tube as the sample vessel and contains all assay reagents pre-packed in tube segments. The unit-dose reagents and internal controls can be held separately in a series of tube segments in the order they are used for an assay by using peelable seals. The peelable seal is formed by a thermal weld of the plastic tube. By applying pressure to the tube segments adjacent to each seal, the seal can burst open to release reagents. In the Liat analyzer, multiple sample-processor modules are aligned with the Liar tube. Each module consists of an actuator and a clamp, whose positions can be controlled to manipulate a test sample within a tube. A retractable magnet is attached to one of the modules for manipulating magnetic beads. When a tube is loaded in the analyzer, the actuators and clamps compress the tube sequentially to move the reagents and controls from one segment to another. Similarly, by synchronizing the motion of the actuators and clamps, various sample processes can be conducted within a tube. Such processes include adjusting a liquid's volume in a segment; releasing a reagent to the adjacent segment; mixing reagents and samples; agitating and incubating a reaction mixture at a given temperature; and washing and removing waste from a segment. Waste is moved toward a waste chamber in the cap while the purified sample moves further down the tube. In the lowest chamber, the released DNA is amplified.

Other commercialized real-time PCR devices intended for field use include the Ruggedized Advanced Pathogen Identification Device by Idaho Technology Inc. (Salt Lake City, the Hand-Held Advanced Nucleic Acid Analyzer by Lawrence Livermore National Laboratory (Livermore, Calif.), and the Bio-Seeq detector by Smiths Detection (Pine Brook, N.J.). However, these devices do not have automated sample preparation and reagent-handling functions.

The systems mentioned above are a step in the right direction. However, the GeneXpert is still moderately complex to operate and has to be operated by a trained technician. Since it requires the user to pipette liquid in the field, a precision measuring instrument would be needed which further increases the cost of the system. Although the Liar Molecular Analyzer does not involve measuring precise liquid volumes in the field, it is expensive because of the complex mechanical system needed to move fluids accurately. The Liat tube is difficult to manufacture, which makes quality control difficult. The tube is difficult to store and has leakage problems.

The controlled movement and delivery of small quantities of molecules such as proteins and chemical reagents represents an ongoing challenge in micro fluidics and is of critical importance for developing POC devices such as the HIV viral load device. The majority of micro fluidic systems rely on fluid motion to move solutions of molecules from one location to another, and as a result, these systems unnecessarily consume solvent and materials and involve complex mechanical systems to control fluid flow. Embodiments of the present invention provide an alternative approach to address the problem in the use of magnetic micro particles as carriers to move molecules from one reaction media to the next and remove all fluid flow from the system. Such an approach where magnetic particles are manipulated using magnetic forces allows one to carry out complex chemical reaction such as viral load testing is a closed cartridge at a low cost. Since the driving force in the reaction is a magnetic field, the system can be automated, allowing for the construction of a portable, reliable instrument for viral load tests with no contamination problems. While the current system is exemplified for sample purification of HIV viral RNA, the platform can easily be extended to other nucleic acid tests and immunoassays, as well as detection of other biological molecules or non-biological molecule of interest.

Embodiments of the present invention provide devices used to perform sample purification and analysis assays in a single instrument. In one exemplary embodiment (See e.g., Example 1) it involves the use of magnetic particles as a solid phase for capture of RNA, subsequent purification and release of RNA to carry out amplification and detection.

Conventional devices conduct assays by exchanging solutions contacting the solid phase. The solid phase may be a micro titer well, a micro particle, or packed column. Even when the solid phase is paramagnetic particles (PMP), assays are typically processed by magnetically capturing the micro particles and exchanging solutions in a single container. Embodiments of the invention use multiple chambers to hold the test sample and water-based or water-alcohol mixture wash buffers and the buffer for carrying out analysis. The water based solutions in the chambers are separated by a lipophilic material (e.g., a wax or oil) which is immiscible with the solutions. This is illustrated, in some embodiments, with a wax material and wells. The wax in the different wells connects to each other forming a wax channel (FIG. 1). The wax can be solidified for storage and transport. During the assay, the wax is melted and the PMP are dragged up into the wax and moved from one compartment to the next by passing them through the wax. Magnetic fields are used to generate the force required to move the PMP and pass them through the interface between the water based solution and the wax. The maximum force is used to move the particles across the interface and a flexible top plate is used to get the magnet close to the interface and reduce the strength of the magnet required to generate the force.

Moving PMP instead of fluids eliminates the need for pumps and aspirators in automated processors and the need of trained technician to aliquot liquids. The use of wax eliminates the need for valves between compartments in single-use test cartridges used in point-of-care analyzers. It also reduces the amount of inhibitors carried over from one chamber to the next by reducing the amount of liquid being carried over from one well to the next. Since the force used to move the particles is magnetic, the system can be completely closed, significantly reducing the risk of contamination, which is a major problem in a sensitive assay such as PCR.

I. Devices

As described above, the present invention provides the ability to produce and use low cost devices for sample preparation and analysis. In some embodiments, the devices are single-use or multiple use and disposable. In some embodiments, the devices utilize a plastic (or other material) cartridge comprising a plurality of sample processing (e.g., sample preparation and/or analysis) wells. Each well comprises a reagent for sample preparation or analysis. The nature of the reagents depends on the particular sample and analysis methods to be employed. In some embodiments, the cartridge is composed of any material that is chemically inert and provides adequate mechanical strength. In some embodiments, the cartridge is constructed using a foil laminate that comprises an aluminum layer for vapor barrier purposes and inert polymer layers in contact with reagents. In embodiments that involve the purification and analysis of RNA (e.g., viral detection or load assays), it is preferred that the cartridge be RNA and RNAse free. Sterilization methods known in the art can be utilized to sterilize cartridges prior to use.

The cartridges of embodiments of the present invention are covered with a material that segregates the sample processing chambers. In some embodiments, the material is any lipophilic material that has phase change characteristics and is immiscible with the reagents for sample preparation and analysis and substances in the sample which can interfere with amplification and detection. In some embodiments, the material is a wax. In some embodiments, the wax is a liquid at room temperature. In other embodiments, the wax is a solid at room temperature and a liquid at a temperature suitable for reactions. In other embodiments, the lipophilic material is an oil. The lipophilic material may be selected as optimal for use with a particular molecule of in crest in terms of temperature use, size exclusion, stability, and the like.

In some embodiments, the lipophilic material separates the sample processing chambers. In other embodiments, the lipophilic material is located in between chambers but does not form the physical barrier between the chambers. In such embodiments, the sample may pass through air or other reagents before or after passing through the lipophilic material.

The present invention is not limited to a particular lipophilic material. In some embodiments, liphophilic materials are immiscible in water and alcohol, exhibit low solubility in water (e.g., ppm), are chemically inert, have melting and boiling points compatible with assay processing (for example, perfluorohexame has a bp of 56° C.), have a specific gravity different from water (e.g., float or sink in water), have a low coefficient of expansion, and are stable at 50° C. for long periods of time (e.g., weeks, months, or years).

Commercially available lipophilic materials that find use in embodiments of the invention include, but are not limited to, Chill-Out 14 wax (MJ Research), paraffin waxes such as IGI 1070A, microcrystalline waxes such as IGI Micosere 5788A, soy and palm waxes such as IGI R2322A, candle waxes such as IGI 6036A, thermoset waxes such as IGI Astorstat 75, hot melt adhesives, atactic polypropylene and polyolefin compounds, petroleum waxes, and dental waxes.

In other embodiments, natural waxes such as animal waxes (e.g., beeswax, lanolin, or) tallow, vegetable waxes (e.g., carnauba, candelilla, and soy) or mineral waxes such as fossil or earth (e.g., ceresin or montan) or petroleum (e.g., paraffin or microcrystalline) waxes are utilized. In yet other embodiments, synthetic (man-made) waxes such as ethylenic polymers (e.g., polyethylene or polyol ether-esters), chlorinated naphthalenes or hydrocarbon type waxes (e.g. Fischer-Tropsch) are utilized.

In some embodiments, oils such as mineral oil, paraffin oil, silicon oil, fluorosilicone, fluorocarbon oil (e.g., Fluorinert FC-40 from 3M), perfluorocarbon fluids (e.g., Flutec® Fluids from F2Chemicals), perfluorodecalin (e.g., P9900 from Aldrich, Flutec PP6, Fluor® Med APF-140HP), perfluoroperhydrophenanthrene (e.g., FluoroMed AFT-215M) or perfluorooctylbromide (e.g., FluoroMed APF-PFOB) are utilized.

Additional barrier materials include, but are not limited to 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, and tetramethylene sulfone (See e.g., Chin et al., Biotechnology and Bioengineering 44:140 (1994); herein incorporated by reference in its entirety). In still further embodiments, ionic liquids (e.g., BMIM[PF6], BMIM[Tf2N] and OMA[Tf2N] where: BMIM-bis(trifluoromethanesulfonyl)imide, PF6=1-n-butyl-3-methylimidazolium hexafluorophosphate, TtN2=bis(trifluoromethylsulfonyl)imide, and OMA=methyltrioctylammonium) are utilized as barrier materials. In yet other embodiments, 1-Butyl-3-methylimidazolium tetrafluoroborate ECOENG™ 21M, 1-Ethyl-3-hydroxymethylpyridinium ethylsulfate, Butylmethylpyrrolidiniumbis(trifluoromethylsulfonyl)imide, ECOENG™ 212, or ECOENG™ 1111P (all available from Solvent Innovations) are utilized as barrier materials.

The reagents provided in the different compartments of the device may be any reagent for performing sample preparation and analysis. Examples include, but are not limited to, cell lysis buffer, wash buffers, affinity reagents, elution buffers, and reaction components for biological assays. The devices of the present invention are suitable for the purification of a variety of biological molecules including, but not limited to, nucleic acids (e.g., RNA, genomic DNA, oligonucleotides and the like), proteins (e.g., peptides, peptide fragments, oligomeric proteins, protein complexes, membrane proteins, and the like), and antibodies. The devices of the present invention are suitable for carrying out any number of biological assays including, but not limited to, amplification of RNA or DNA (e.g., PCR, TMA, NASBA), detection of nucleic acids (e.g., hybridization assays), and immunoassays.

In some embodiments, the device includes a component to transport sample from one compartment of the device to the next. In some embodiments, samples are associated with magnetic beads and the transport component is a magnet. In other embodiments, the transport component generates electric current to transport sample. In still further embodiments, centrifugal force is utilized to transport sample and the transport component generates such force (e.g., by movement of the device). In other embodiments, a fluid with a specific gravity greater than water is used such that the fluid moves without mechanical intervention.

In some embodiments, the device includes a detection component to detect a labeled or otherwise presence biological sample or assay product. Examples include, but are not limited to, spectrophotometers, mass spectrometers, NMR, microscopy and the like. In some embodiments, products are read directly from the final compartment of the device (e.g., using a window for spectroscopy). In other embodiments, products are removed from the device (e.g., using an automated component of the device) for detection.

Embodiments of the present invention further provide a device comprising fluidic chamber of reactants (e.g., a vertical column) separated by a "wall" of lipophilic material which prevents the reactants from mixing but allows microparticles to cross (e.g., magnetic particles transported by a magnet).

In some embodiments, the device and its use are automated. An automated system comprises a device for sample purification and analysis, a transport component for moving sample through the device, and any additional components necessary, sufficient or useful for the automation of the process (e.g. pre-processing reagents and sample transport or post analysis detection or further analysis components). In some embodiments where magnetic transport is utilized, the transport component comprises a magnet that moves between chambers of the device. In other embodiments, the device moves relative to a stationary magnet or other transport device.

II. Methods

As described above, the present invention provides sample preparation and analysis devices and methods of using the devices.

A. Sample

Any sample suspected of containing the desired material for purification and/or analysis may be tested according to the disclosed methods. In some embodiments, the sample is biological sample. Such a sample may be cells (e.g. cells suspected of being infected with a virus), tissue (e.g., biopsy samples), blood, urine, semen, or a fraction thereof (e.g., plasma, serum, urine supernatant, urine cell pellet or prostate cells), which may be obtained from a patient or other source of biological material, e.g., autopsy sample or forensic material.

Prior to contacting the sample with the device or as a component of the device or automated system, the sample may be processed to isolate or enrich the sample for the desired molecules. A variety of techniques that use standard laboratory practices may be used for this purpose, such as, e.g., centrifugation, immunocapture, cell lysis, and nucleic acid target capture.

In other embodiments, the methods of embodiments of the present invention are utilized to purify and/or analyze intact cells (e.g., prokaryotic or eukaryotic cells).

B. Purification Methods

In some embodiments, the devices of the present invention are utilized in sample preparation and purification. Any suitable methods for purification may be utilized, including but not limited to, target capture, washes, precipitations and the like. In some embodiments, sample purification is carried out entirely in the device and does not require any additional purification steps. Purification may occur in one or more reaction chambers. This decreases the complexity of purification and reduces cost. One of skill in the art recognizes that the particular purification method is dependent on the nature of the target biological sample.

C. Modification/Analysis/Detection

The purified sample may be detected using any suitable methods, including, but not limited to, those disclosed herein. The description below provides exemplary techniques for biological molecules such as nucleic acids and proteins. Other techniques may be applied for biological molecules or non-biological molecules, as desired or needed.

i. Nucleic Acid Detection

Examples of nucleic modification/analysis/detection methods include, but are not limited to, nucleic acid sequencing, nucleic acid hybridization, and nucleic acid amplification. Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing. Illustrative non-limiting examples of nucleic acid hybridization techniques include, but are not limited to, in situ hybridization (ISH), microarray, and Southern or Northern blot. Nucleic acids may be amplified prior to or simultaneously with detection.

Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g. PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al. *Bio Technol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified target nucleic acids can be detected by any conventional means. For example, target in RNA can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an aeridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/ quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and many types of interacting label pairs are known (e.g., U.S. Pat. No. 6,534,274, herein incorporated by reference in its entirety).

Another example of a detection probe having self-complementarity is a "molecular beacon" (see U.S. Pat. Nos. 5,925, 517 and 6,150,097, herein incorporated by reference in entirety). Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL, and EDANS).

Other self-hybridizing probes are well known to those of ordinary skill in the art. By way of non-limiting example, probe binding pairs having interacting labels (e.g., see U.S. Pat. No. 5,928,862, herein incorporated by reference in its entirety) may be adapted for use in the compositions and methods disclosed herein. Probe systems used to detect single nucleotide polymorphisms (SNPs) might also be used. Additional detection systems include "molecular switches," (e.g., see U.S. Publ. No. 20050042638, herein incorporated by reference in its entirety). Other probes, such as those comprising intercalating dyes and/or fluorochromes, are also useful for detection of amplification products in the methods disclosed herein (e.g., see U.S. Pat. No. 5,814,447, herein incorporated by reference in its entirety).

In some embodiments, detection methods are qualitative (e.g., presence or absence of a particular nucleic acid). In other embodiments, they are quantitative (e.g., viral load).

ii. Protein Detection

Examples of protein detection methods include, but are not limited to, enzyme assays, direct visualization, and immunoassays. In some embodiments, immunoassays utilize antibodies to a purified protein. Such antibodies may be polyclonal or monoclonal, chimeric, humanized, single chain or Fab fragments, which may be labeled or unlabeled, all of which may be produced by using well known procedures and standard laboratory practices. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). In some embodiments, commercially available antibodies are utilized.

D. Data Analysis

In some embodiments, following purification and detection, a computer-based analysis program is used to translate the raw data generated by the detection assay (e.g., the presence, absence, or amount of a given target molecule) into data of predictive value for a clinician or researcher. In some embodiments, the software program is integrated into an automated device. In other embodiments, it is remotely located. The clinician can access the data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

Any method may be used that is capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw data, the prepared format may represent a diagnosis or risk assessment (e.g., viral load levels) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. Compositions & Kits

In some embodiments, systems and/or devices of the present invention are shipped containing all components necessary to perform purification and analysis (e.g., pre-loaded into the device). In other embodiments, additional reaction components are supplied in separate vessels packaged together into a kit.

Any of these compositions, alone or in combination with other compositions disclosed herein or well known in the art, may be provided in the form of a kit. Kits may further comprise appropriate controls and/or detection reagents, Any one or more reagents that find use in any of the methods described herein may be provided in the kit.

EXPERIMENTAL

The following examples are provided to demonstrate and illustrate certain preferred embodiments and aspects of the compositions and methods disclosed herein, but are not to be construed as limiting the scope of the claimed invention.

Example 1

This example described moving paramagnetic micro particles using magnetic forces to capture RNA, subsequent purification, and release of RNA for amplification and detection. It also shows the use of liquid wax, as an exemplary lipophilic material, as a valve between the various chambers allowing for the movement of paramagnetic micro particles while forming a barrier between the various wash buffer.

(a) Fabrication of the Cartridge

Individual cartridges for the assay were prepared by machining a sterile, clear round bottom polystyrene 96 well plate (FIG. 1a). The wax channel was made using FDA compliant plain back 1/16" polypropylene sheets, In order to fabricate the wax channel, 9495 LE acrylic adhesive transfer tape (3M, St. Paul, Minn.) meant for low surface energy substrates was glued onto both sides of a rectangular piece of plastic cut to the correct dimensions. A rectangular channel was milled out of the plastic piece. The milling process also cut the adhesive. In view of the poor thermal conductivity and low melting point of polypropylene, special care has to be taken while machining it. The burrs forming during machining of the channel were removed using a razor blade. The top plate is also made out of a polypropylene sheet. Tiny holes were punched on the top plate to allow for the introduction of fluids.

Polypropylene was used for the top plate and the channel because of its excellent chemical resistance. The saturated olefinic chains yield resistance to most oils and solvents, as well as water-based chemicals, soaps, and moderate acids and bases. Few other materials with the strength properties of polypropylene match the chemical resistance of polypropylene. Also, polypropylene's hard, high-gloss surface makes it desirable for environments where there is concern for build-up that can interfere with flow sterilization of the cartridge: it is preferred that a RNA free environment is maintained throughout the test. While commercially available plastic parts are radiated with gamma rays to sterilize them, a protocol was developed to sterilize the plastic parts which could be easily carried out in a laboratory setting. The wells to be used for the test were sealed off using adhesive tape before machining the plate. After the completion of machining, the cartridge was washed using the following protocol:

a. wash twice with water
  b. wash twice with 100% ethyl alcohol
  c. wash with RNaseZap® RNase Decontamination Solution (Ambion, Austin, Tex.)
  d. wash twice with water After the washing was complete, the cartridge was dried overnight at 50° C.

RNA Purification Assay:

The assay was performed using 400 μL, of plasma sample containing $10^6$ copies/mL Armored RNA (Abbott Molecular, Des Plaines, Ill.). Armored RNA is used instead of naked RNA as a test sample because it is ribonuclease resistant and easily quantifiable by copy number of RNA. It is also noninfectious, making it easy for to handle.

In order to purify RNA from a plasma sample, the Mag-MAX Viral RNA Isolation Kit (Ambion, Austin, Tex.) was employed. In this method, the cells are disrupted using the classic method of guanidium thiocyanate-based solution. This simultaneously releases the viral RNA and deactivates the nucleases in the sample matrix. The RNA then binds to the silica coated magnetic beads in the presence of a chaotropic agent and alcohol. The beads are then washed and eluted in aqueous low salt buffer.

Preparation of Lysis/Binding Solution and Bead Mix: Carrier RNA is Added to the lysis/binding solution concentrate according to Table 1 and mixed briefly. This is followed by the addition of 100% isopropanol. In order to prepare the bead mix, 10 μL of RNA binding beads are mixed with 10 μL of lysis enhancer for every reaction. The beads are vortexed before aliquoting.

TABLE 1

| Volume of reagents to be added to prepare lysis buffer | |
|---|---|
| Reagent | Amount |
| Lysis/Binding soln. Concentrate | 400 μL |
| Carrier RNA | 2 μL |
| 100% isopropanol | 400 μL |

Preparation of the Cartridge

802 μL of the lysis solution was added to a microfuge tube along with 400 μL of plasma sample containing armored RNA. When adding sample, the pipette tips should be immerged slightly into the solution to prevent aerosol formation leading to contamination. The solution is vortex mixed gently for 30 seconds and then 20 μL of bead mix is added to the tube. The solution is vortex mixed gently for 4 minutes on a vortex mixture to fully lyse the viruses and bind RNA to the magnetic beads. The beads are captured by leaving the microfuge tube on a magnetic stand. 600 μL of the solution is removed and discarded away. The beads are vortex mixed in the remaining 222 μL of solution. This solution is aliquoted into the first chamber of the cartridge. 150 μL of wash buffer 1 containing isopropanol is added to chamber two and three respectively. 225 μL of wash buffer 2 containing ethanol is added to chamber four and five respectively, 50 μL of elution buffer is added to chamber 6.

The wax channel (FIG. 1-b) is now glued onto the cartridge by peeling off the paper laminate of the adhesive transfer tape attached to the wax channel and applying the wax channel to the cartridge. This is followed by the adhesion of the top plate to the wax channel following a similar process. Chill-Out Liquid Wax (Bio-Rad Laboratories, Hercules, Calif.) is then pipetted into the cartridge through the punched holes of the top plate till there is no air gap remaining in the cartridge. FIG. 1 shows the image of the completely filled cartridge with the different buffers and the wax.

Figure 2:
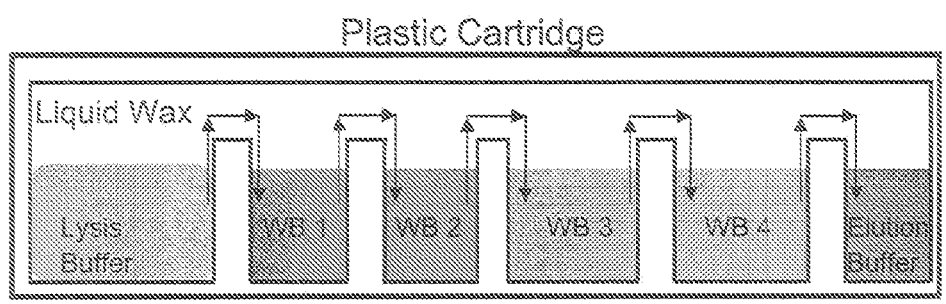
FIG. 2 shows a cartridge for sample purification of some embodiments of the present invention.

Sample Purification Protocol (a) Purification in the cartridge. In the sample purification process, a magnetic force is used to carry out the various purification steps (FIG. 2), for example, magnetic separation of the beads to accumulate them into a clump, movement of the particles from the buffer to the wax, movement of the particles in the wax, reintroduction of the particles into the next buffer and agitation of the particles in the buffer (Sample C1 in table 2). This magnetic force is produced by a permanent magnet. The clump of particles was moved from lysis buffer in chamber 1 to elution buffer in chamber 6 through the various wash buffers in chambers 2-5. The particles were allowed to sit for 30 seconds in each wash buffer, and for 10 minutes in the elution buffer. The particles were moved magnetically in the buffers during these times.

(b) Purification in a microfuge tube. The sample purification was carried out using the Ambion MagMax kit in a microfuge tube as well. In this case, the microfuge tube containing the lysis buffer and the RNA binding PMPs was put on a magnetic stand to capture the PMPs. Once capture in complete, the RNA binding beads formed a pellet against the magnet in the magnetic stand. The supernatant is aspirated out without disturbing the beads. The tube was removed from the magnetic stand, and Wash buffer 1 was added to it. The solution was agitated for 30 seconds. A similar process of capture and aspiration was carried out. The beads were washed twice with Wash Buffer 1 and twice with Wash Buffer 2. In this study, two different combinations of wash buffer volumes were used: (i) 300 µL of wash buffer 1 and 450 µL of wash buffer 2 (sample C2 in table 2) (ii) 150 µL of wash buffer 1 and 225 µL of wash buffer 2 (sample C3 in table 2) After the 4 wash steps the beads were left open at room temperature to allow the remaining alcohol to evaporate. The tubes were inspected for any remaining alcohol since alcohol inhibits PCR. 50 µL of elution buffer was added and the sample agitated vigorously for 4 minutes, in each case, the particles are captured after elution and 12.5 µL of the sample was used for RT-PCR using the Abbott Real time Assay.

Results and Data Analysis

The table shown below shows the average Ct values for the three Sample types

TABLE 2

Samples and the Ct values for the

| Sample | Average Ct value |
|---|---|
| Prototype cartridge + reduced wash buffer (C1) | 15.2 |
| Ambion kit protocol in microfuge tube | 16.7 |
| Ambion kit in microfuge tube + reduced wash buffer (C3) | 20.1 |

The data shows that there is a 2.8 fold (2^mean Ct difference) improvement in RNA purification when the particles are moved through wax. This occurs in spite of the reduction in the wash buffer volume. Comparing the results with a similar volume of wash buffer, there is a 30 fold improvement in RNA purification. In the manual approach of sample purification, a significant amount of solution would adhere to the particles, which cannot be aspirated out. Therefore, while each wash step leads to the dilution of the inhibitors which are carried from the lysis solution, it would take a significant number of washes and wash buffer volume to dilute out all the inhibitors completely. While using wax as a medium of particles transport, the amount of liquid being carried is significantly lower which leads to an improvement in Ct.

Effect of Alcohol on RT-PCR

Alcohol is a known inhibitor of PCR. Therefore, the Ambion sample purification kit requires drying the particles in air before eluding the RNA. In the new protocol described herein, the drying step is completely removed. Again, this shows that the amount of fluid being carried from one chamber to the next is minimal. It also simplifies the sample purification process significantly allowing for easy automation. The presence of smaller quantities of inhibitors also allows for elution in smaller quantities of elution buffer, which in turn speeds up the thermal cycling speed, thereby reducing the time required to carry out the test.

Example 2

Automation

An inexpensive automated sample purification system is developed by moving magnetic particles instead of fluids. A cartridge which can hold fluid through long periods of storage is designed. This does away with any sort of pipetting in the field. Optimization of the assay in this novel platform enables one to improve the sample purification process and develop a better understanding of the system. An automated system for carrying out the purification allows for the measurement of viral load without the need of highly trained lab technicians. The combination of a closed cartridge and automated device would create a point of care platform not only for viral load, but for all kinds of nucleic acid testing in a cheap, convenient manner with a reduced risk of cross contamination.

Experiments to optimize the system include:

a Fabricate a cartridge using foil laminate to hold the chemicals for storage and to carry out reactions.

b Optimization of the sample purification protocol in new cartridge.

c Build a robust automated system to remove man-power requirements a. Fabricate a Prototype Cartridge to Carry Out Sample Purification There are two parts to this fabrication: (a) Material used to make the cartridge (b) design of the cartridge itself.

(a) Material. The material to be used to make the cartridge preferably provides (a) a vapor barrier to hold the liquids through long periods of storage without significant loss. (h) mechanical strength; and (c) a chemically inert surface which does not stick to the blood or particles present in the solution.

While polystyrene or polypropylene is the choice of material for carrying out chemical assays because of their chemical inertness, they do not provide the vapor barrier needed to store the reagents for long periods of dine. The vapor barrier of a material is measured in terms of water vapor transmission rate (WVTR) which is a measure of the passage of water vapour through a substance.

WVTR=$\Delta w/\Delta t$ A (g m$^{-2}$ s$^{-1}$), Where $\Delta w/\Delta t$ is the amount of moisture loss per unit of transfer (g s$^{-1}$) and A is the exposed area to moisture transfer (m$^2$)

TABLE 3

WVTR characteristics of some common plastics

| Material | Density (g/cm3) | Thickness (mil) | WVTR[a] | WVTR[b] |
|---|---|---|---|---|
| Ultra Low density poly Ethylene | 0.9015 | 10 | 0.3313 | 0.846 |
| Low density poly ethylene | 0.9188 | 2 | 0.17 | 0.4274 |
| High density poly ethylene | 0.9433 | 2.5 | 0.053 | 0.136 |
| Poly propylene | 0.8994 | 2.5 | 0.1015 | 0.2738 |
| Rollprint foil laminate | 2.1011 | 3.5 | 0 | 0 |

Figure 3:
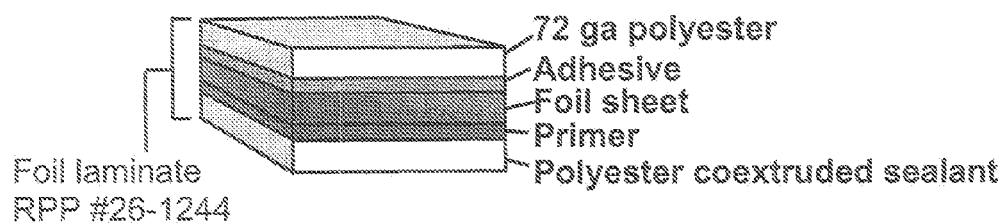
FIG. 3 shows layers of a foil laminate used in constructing cartridges of some embodiments of the present invention.

[a]g/mil/100 sq in/day at 30° C. and 35% RH
[b]g/mil 100 sq in/day at 40° C. and 35% RH Table 3 shows table below shows the WVTR of some plastics and of a foil laminate (RP/26-124.4, Rollprint, Addison, Ill.). It is evident that foil laminate provides excellent vapor barrier for reagents during storage. Foil laminate has the added benefit of being extremely inexpensive. The cost of a single cartridge made out of foil laminate would not exceed a few cents. The various layers of foil laminate to be used are shown in FIG. 3 below.

The foil laminate (Rollprint Packaging Products, Addison, Ill.) contains a 2 mil Aluminum layer which is responsible for the low WVTR making it ideal for the storage of reagents. The polyester layer provides a chemically inert and hydrophobic surface preferred for carrying out the assay. It also allows the foil to be heat sealed to another piece of foil or plastic. The nylon outer surface protects the aluminum surface from corrosion and also provides mechanical strength to the foil laminate. The foil laminate lacks rigidity. This can be overcome by packaging it in a rigid material. It should be noted that while the foil laminate is virtually impermeable to vapor, the seal between two layers of foil is not and is responsible for some loss of vapor.

In other embodiments, a vacuum formed chamber made out of polypropylene or polystyrene similar to a 96 well plate is used. In some embodiments, in order to provide a vapor barrier, this would be aluminized by vapor deposition.

Figure 4:
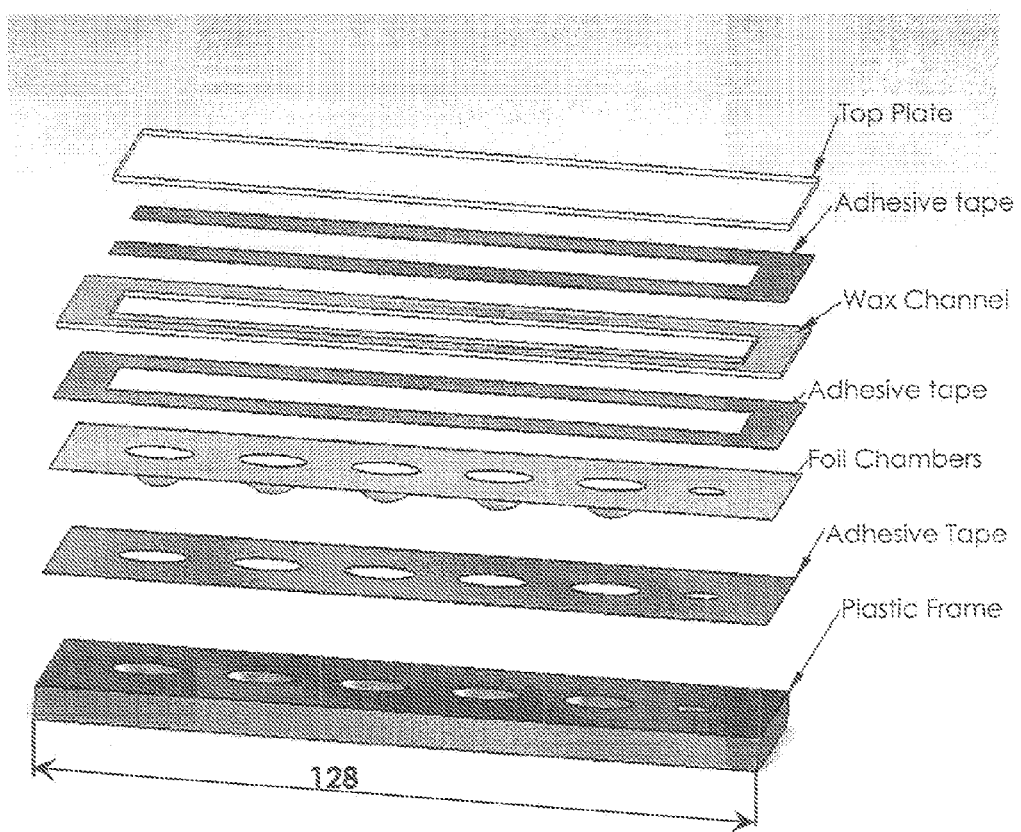
FIG. 4 shows a drawing of a foil laminate cartridge used in some embodiments of the present invention.

(b) Shape and size of the cartridge. While the shape of the chambers are governed by the various forces acting to move the particles and the needs to simplify the automation, the size of the chambers is governed by the chemistry associated with sample purification. The prototype designing is done using a 3D Mechanical CAD program, Solidworks (Solidworks Corporation, Concord, Mass.). An example of a cartridge based on the currently used volumes is shown in FIG. 4. Changes in the chemistry or automation needs are accommodated by changing the shape and size of the chambers accordingly.

(c) Peelable layer and top plate: The top plate of the cartridge is preferably transparent in order to make optical readings during the thermal cycling. Not shown in the drawing is a peelable foil laminate layer which sits between the top plate and the foil chambers. This is similar to a printer ink cartridge. The end of the peel comes out between the top plate and the wax layer. This provides the vapor barrier optimum for long term storage. Solid wax is present above and below the seal. The wax below allows for the peel to be removed without risk of loss of reagent sticking to the peel. Before the test, the peel is removed and the wax melted. The top plate can be made flexible which allows us to compress it to remove any air gap that forms because of the cavity created by the removal of the seal. It also should be chemically inert since it comes in contact with the particles when they are dragged from one chamber to the next. The peelable seal is heat sealed to the chambers. The distance between the chambers is preferably 6 mm to allow for proper sealing, although other dimensions may be used. This sealing process is carried out in Rollprint Inc.

Fabrication. The fabrication of the aluminum foil cartridges is done using a pinch press device that comprises a positive hemispherical head which fits into a negative mold of the same size. By pressing the foil between the positive head and the negative mold, the foil is stretched to confirm with the shape of the mold. While the yield strength and the tensile strength of the laminate are not known, the standard industry practice is:

(Maximum area after making the chamber)<(2×area before extension)

The wax channel, the solid support, for cartridge, the top plate is all joined together using 3M adhesive transfer tape. Several adhesives were tested before choosing this one because of its excellent adhesion properties, especially to low surface energy surfaces. The adhesive is laser cut to the correct size by GML (Vadnais Heights, Minn.). Optimization of sample purification protocol to improve assay performance:

The assay is performed using a silica coated PMP based MagMax kit from Ambion. The kit protocol is optimized for best performance in an assay format which involves sedimentation of the beads and pipetting out of the fluid. It is not meant to be used with the wax. In order to further understand the effects of the wax on the sample purification and to optimize the sample purification process, the following experiments are carried out:

1. Carryover of water through the wax: Based on the initial experiments, it was hypothesized that the carry-over of water or buffer from one chamber to the next is reduced significantly on moving the particles through the wax. This was based, in part, on the results described above, which show the lack of inhibition due to alcohol, in order to confirm this hypothesis, a known concentration of a fluorescent dye, fluorescein is dissolved in water. A known number of particles (as measured on a Luminex flow cytometer) is added to this solution. Then, the particles are magnetically moved through the wax into a known volume of fluorescein free water. On measuring the concentration of fluorescein in the starting sample and the final sample, one can quantitatively estimate the volume of water being carried over from one chamber to the next ($V_a$).

The experiment has two controls which are used to compare the results: (a) move the particles with a pick-pin from an identical solution of fluorescein to water. This represents currently available systems such as the Maxwell or Kingfisher, (b) Collect the particles by putting the microfuge tube containing the fluorescein solution and the particles on a magnetic stand and then carefully pipetting out the solution. This is followed by the addition of a fixed quantity of fluorescein free water.

An improvement in purification performance is quantified by comparing the average volume of liquid carried across from one chamber to the next. The variance is used to quantify the variability in the purification process due to sample handling. The experiment is repeated for different number of particles, different initial volume of sample, and different fluorescein concentrations. The volume of liquid being carried across is a fraction $\phi$ of the volume of the droplet (V) containing the particles which moved into the wax.

$$(1-\phi)V=(4/3)\pi r^3 N$$

$$\phi V = V_a$$

$$\phi = V_a/(V_a + 4\pi r^3 N)$$

In the above equations, r is the radius of the particles and N is the total number of particles. The volume of the droplet V is dependant on N and therefore the volume of liquid $\phi V$ is also dependant of N. One would not expect $\phi V$ to be dependent on the initial volume of fluorescein solution, but rather on the concentration of fluorescein. This experiment allows one to determine the optimal wash steps and volume, or the volume of the lysis buffer required.

2. Selecting optimal wash step volume and number. The protocol recommended by Ambion is optimized for a manual pipetting procedure. It does not account for the presence of the wax. Therefore, the protocol is optimized using wax. While all the inhibitors present in blood plasma which inhibit PCR are not known specifically, it is accepted that inhibition by most inhibitors is concentration dependant. The results from the previous experiments provide information about the effect of the wax on the removal of fluids. Using that as a guide stick, the number of purification steps is reduced. The reduction in the number of purification steps reduces the complexity of the sample purification process, reduces the cost of the test and the time required for the test. A reduction in the inhibitor concentration allows for elution in a smaller volume of elation buffer, leading to a further increase in the RNA concentration and faster thermal cycling.

The sensitivity of a method is associated with the lower limit of applicability of that method, in relation to chemicals, the minimum detectable value often refers to the minimum detectable net concentration or amount.

Determination of the LOD

Calculation of the LOD differs between professional scientific bodies and between different applications, but one definition of the LOD is:

$$LOD \cdot (\text{mean of blanks}) + K(sd)$$

Where mean of blanks=the mean value given to the blank determinations associated with an assay; K=coverage factor associated with a desired confidence level; and sd=standard deviation of the blank determinations.

This calculation is unsuitable for estimating the LOD associated with real-time quantitative PCR methods as the blank controls typically have values equal to the highest cycle number used in the PCR reaction. Additionally, if the assay has worked correctly, the value of these blanks will all be the same and their distribution truncated, thus precluding the calculation of a useful standard deviation.

In order to overcome some of the difficulties encountered with the traditional calculation of LOD described in the scientific literature, one can define the LOD as the lowest copy number that gives a detectable PCR amplification product at least 95% of the time. This can also be interpreted as the lowest copy number that can be distinguished from the background noise with a probability of 95%. The current Rt-PCR assay using the Ambion kit for RNA purification and Abbott Real time protocol for Rt-PCR has been reported to have an LOD of 40 copies of RNA in 1.0 ml of plasma sample. Preferred assays detect a minimum of 500 copies of RNA. Thus, for every protocol, the sensitivity of the assay is measured by creating a dilution curve of Ct verses copies of RNA. The desired goal is to go from the lysis buffer to the elution buffer without a single wash step. The purification assay is carried out with different number of wash steps and wash volume.

3. Wax Melting Point

The wax that used in the experiments described in Example 1 has a melting point of 10 C. Therefore, this wax is liquid at room temperature. A wax (DyNAwax Reagent, Finland), which melts at 60 C or other higher melting temperature was is used in some embodiments. This allows for storage of the wax as solid during storage with subsequent melting just before the experiment, thereby creating a phase change plug for the movement of particles. The other advantage is that the presence of wax below the peelable seal allows one to peel the foil without losing any fluid from the chambers which might have stuck to the foil. However, this would involve carrying out the experiment in a water bath or using a peltier heater to heat the wax.

Automation of the Sample Purification Protocol:

An automated sample purification system is provided. Automation has numerous benefits, namely: (a) the process does not require a skilled worker, (h) provides for better understanding of the system, (c) speeds up the assay development and testing process, (d) reduces sample to sample variations by standardizing the process.

Figure 5:
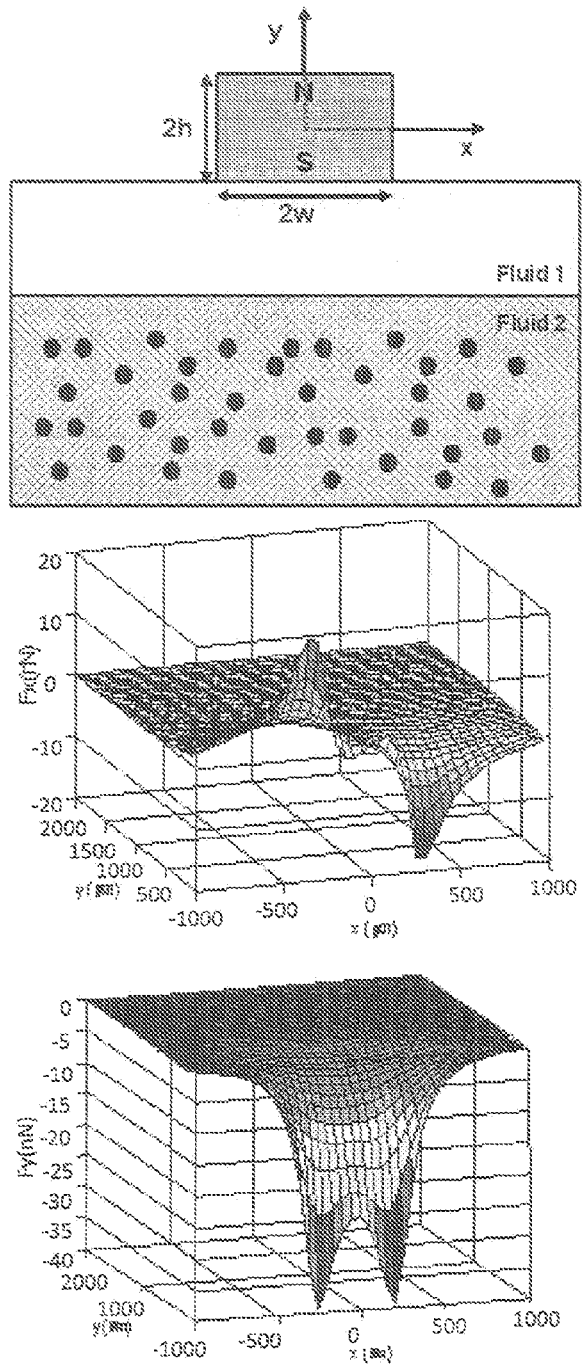
FIG. 5 shows (a) the position of a permanent magnet with respect to two immiscible fluids and (b) a surface plot of magnetic force on a particle in the x and y directions.

(a) A first component is a stage to move magnets and cartridge. In order to automate the process, a stage is built to carry out the five processes, namely (a) Aggregation of the particles in a fluid (b) dragging the fluid across the interface (c) dragging the particle aggregate in the wax (d) dragging the particle aggregate from the wax to the water (e) agitating the particles in the fluid. In the manual mode of operation, the cartridge was held steady while the magnet was displaced relative to the cartridge. In order to create the complex motion automatically, in some embodiments, the cartridge is moved with respect to the magnets. Thus the magnets and/or the cartridge are mounted on a moving stage. The decision on which to move is dependent on ease of construction, cost and reliability of the process. Stepper motors may be used to carry out the various movements.

i) Aggregate the particles in the wash buffer. The design is guided by a simple estimation of the forces involved. The motion of a spherical magnetic particle of density $P_p$, radius $R_p$, volume $V_p=(4\pi Rp^3)/3$, and mass $m_p$ is governed by several forces including, (a) the magnetic force due to all field sources, (b) fluidic drag, (c) particle/fluid interactions (perturbations to the flow field), (d) buoyancy, (e) gravity, (g) thermal kinetics (Brownian motion), and (h) inter-particle effects such as magnetic dipole interactions. In order to guide the design parameters, the behavior of magnetic particles in low concentration and slow flow regimes where the magnetic and viscous drag forces dominate is modeled. Therefore, particle/fluid interactions and interparticle effects are ignored. The gravitational force, which while of second order might not be negligible depending on the particle size, is included. According to classical al Newtonian dynamics:

$$m_p = dv_p/dt = F_m + F_f + F_g,$$

where, $v_p$ is the velocity of the particle, and $F_m$, $F_f$ and $F_g$ are the magnetic, fluidic, interfacial and gravitational forces, respectively. The magnetic force is obtained using an "effective" dipole moment approach where the magnetized particle is replaced by an "equivalent" point dipole with a moment $m_{p,eff}$ (Furlani and Ng, 2006). The force on the dipole and hence on the particle) is given is given by:

$F_m = \mu_f(m_{p,eff} \cdot \nabla)H_a$, where $\mu_f$ is the permeability of the transport fluid, $m_{p,eff}$ is the "effective" dipole moment of the particle, and $H_a$ is the (externally) applied magnetic field intensity at the center of the particle, where the equivalent point dipole is located. If the particle is in free-space, $m_{p,eff} = V_p M_p$ and the above equation reduces to the usual form $F_m = \mu_0(m_p \cdot \nabla) H_a$, where $V_p$ and $M_p$ are the volume and magnetization of the particle, and $\mu_0 = 4\pi \times 10^{-7}$ is the permeability of free space. FIG. 5 shows the arrangement of a magnet above the fluidic chamber and the surface plot of force on a particle in the x direction and the y direction at a fixed distance from the magnet. The force calculation requires a choice of particle size and material properties of, $Fe_3O_4$ (magnetite), which make up the particles. In the calculation shown, it was assumed that $Fe_3O_4$ has a density $p=5000$ kg/m$^3$, a saturation magnetization of $M=4.78\times10^5$ A/m and the particle size is 0.5 micrometer. A program was written in Matlab to estimate the magnetic force for a system consisting of one magnet or an array of magnets. This enables one to calculate the magnetic force for different magnets and arrangements of magnets. While the current program can only estimate forces due to a linear array of magnets, it is possible to generate a program to estimate a more complex arrangement of magnets.

The fluidic force is predicted using the Stokes' law for the drag on a sphere in uniform flow, $F_f = -6\pi\eta R_p(v_p-v_f)$, where $\eta$ and $v_f$ are the viscosity and the velocity of the fluid, respectively. The gravitational force is given by $F_g = -V_p(\rho_p-\rho_f)g\hat{y}$, where $\rho_p$ and $\rho_f$ are the densities of the particle and fluid, respectively, and g=9.8 m/s² is the acceleration due to gravity. The gravitation force acts in the -y direction. The gravitational force is often ignored when analyzing the magnetophoretic motion of submicron particles, as it is usually much weaker than the magnetic force.

Plugging the various forces into Newton's equation of motion, it is possible to predict the approximate time it would require for the particles to aggregate and even plot the particle trajectories. These calculations are used to guide the design parameters.

(ii) Measure the surface tension and drag the particles across the interface, The strength of the magnet used in the automated process is governed by the strength of the magnetic field required to overcome the interfacial surface tension. While it is difficult to move one particle across the interface, a particle clump can be moved across the interface.

The interfacial force can be estimated as $y2\pi R_p$ where y is the interfacial tension between wax and buffer. The interfacial force is measured using the weight drop method which follows from Tate's law.

Figure 6:
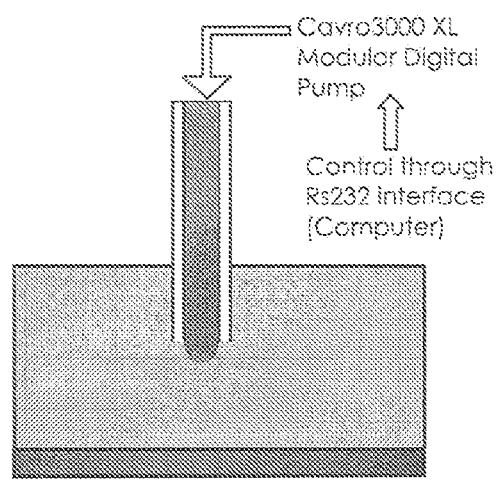
FIG. 6 shows an experimental set up for estimation of surface tension using the weight drop method.

This is an accurate method of determining surface tension and perhaps the most convenient laboratory one for measuring surface tension of a liquid-air or liquid-liquid interface. As illustrated in FIG. 6, the procedure is to form drops of the wax at the end of a tube, allowing them to fall into a container containing buffer. The weight of the drop is then used to determine the surface tension. Tates law gives a very simple expression for W, the weight of a drop minus the displaced fluid: $W=2\pi ryf$, where is the radius of the tube from which the drop forms and f is a function of the dimensionless ratio of $r/V^{1/3}$, where V is the drop volume. The system shown in FIG. 6 is used to measure the surface tension between the wax and the various wash buffers. An important precaution to be taken when employing this method is to use a tip that has been ground smooth at the end and which is free from any nicks, in the case of liquids that do not wet the tip, r is the inner radius. The drops should also be formed slowly otherwise the drop weight will be high.

Having estimated the interfacial force, one can estimate the magnetic force required to move the particles across the interface. Therefore, the design criteria is: $F_m > F_i$, where $F_m$ and $F_i$ are the magnetic and interfacial forces respectively. This estimation neglects frictional force as well. This estimation guided the choice of magnet. In order to reduce the strength of the magnet required to move the particles from the buffer to the wax, the magnet is moved as close to the interface as possible. This is done with a flexible top plate. A flexible top plate is also used so that it can be depressed to remove any air gaps which may form when the foil laminate which lies between the chambers and the top plate is peeled off.

iii) Drag the particle aggregate across the wax. The equation of motion for dragging the particles through the wax is similar to that of aggregation of the particles. However, in this case, the motion is that of a droplet of fluid containing a particle aggregate rather than that of a single particle. The net frictional force is given by $F_f = -6\pi \eta R_p (v_p - v_f)$, where $R_p$ is the translational tensor which depends on the shape of the droplet and the internal viscosity of the droplet. It is fairly easy to drag the particle aggregate through the wax. During this process, the particles come in contact with the top surface of the cartridge. It is therefore preferred that the material used for the top plate process is chemically inert and has a smooth surface texture.

(iv) Drag the particle aggregate from the wax to the buffer. Since the movement of particles from the wax to the wash buffer is accompanied by a decrease in surface energy, this is a simple process. A small magnetic force is sufficient to drag the particles back into the water. Also, the gravimetric force aids the process of the particle settlement.

(v) Verify the need for agitation: In the assay performed in Example 1, the particles were agitated by moving a magnet around the chamber. This was done since the sample purification process involving manual pipetting required agitation of the particles in the wash buffer by vortex mixing. While creating a variable magnetic field is possible by moving magnets on a stage, it adds to the cost of the assay. Thus, in some embodiments, agitation is not used.

Software to control the movement of the stepper motors and the cartridge. The USB port of a computer can be connected to a stepper motor controller via a USB to RS232 converter. This allows one to send commands to the motor using the hyper terminal. Any serial communication software such as Docklight can be used to effectively communicate with the stepper motor using RS232 command sets.

Test the performance of the automated sample purification system. In order to test the performance of the sample purification system, the loss of particles is measured. This is compared to a loss of performance in the manual form of the assay and the assay with pipetting of fluids. For this purpose, the particle concentration is measured using the Luminex flow cytometer. Unlike ordinary flow cytometers, the Luminex system has a positive flow control system which allows one to count particles as well as measure the volume of solution used, thereby enabling one to measure the concentration of the bead solution. Loss of beads=Initial concentration of bead×Vol of sample used−final concentration of beads×Vol of elution buffer.

% loss of beads=(Loss of beads/Total initial number of beads)×100

The percentage loss of beads is measured at each stage of the automation process to measure the performance of the system. The aim is to reduce the percentage loss to less than what is observed in a manual process. The mean % loss of beads and the variance of % loss of beads are compared for the automated process and the manual approach. An automated system is expected to have a lower variance than a manual process.

Example 3

Tubular Processor

Figure 7:
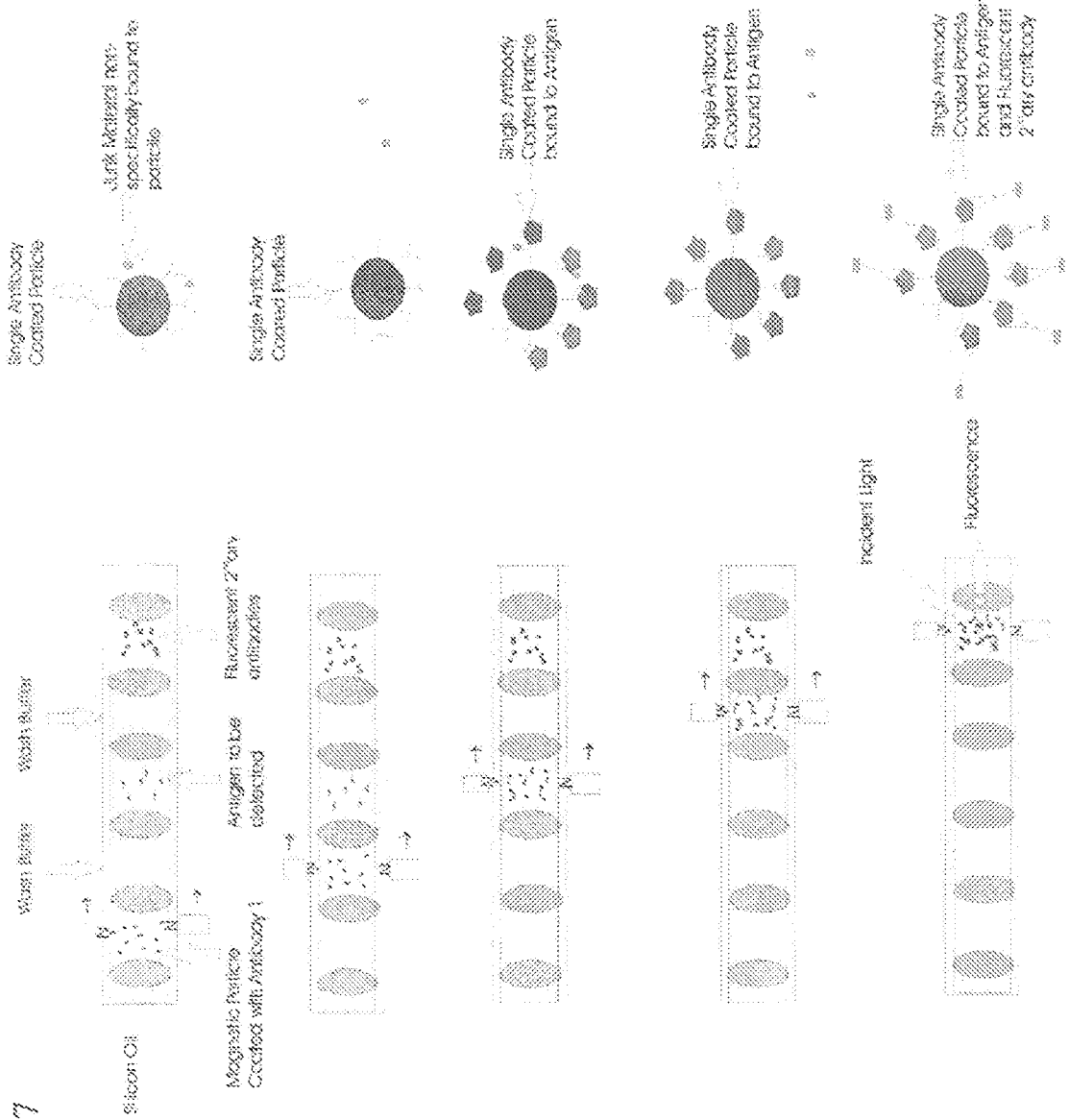
FIG. 7 shows an illustration of the various stages of a sandwich assay in a tube-based microfluidic system.

This example describes a tubular processor for performing biological reactions. The experimental setup for the diagnostic assay is shown in FIG. 7. It consists of a 0.060" internal diameter tube (Small Parts Inc.) attached to a CAVRO 3000XL digital pump. The digital pump is controlled through an RS232 interface. The different wash buffers, analytes, solution containing magnetic particles and silicone oil (Gelest Inc.) are pumped in from the distal end of the tube.

The particles used for the experiment are carboxyl coated smooth surface magnetic particles obtained from Spherotech Inc. The SPHERO™ Smooth Surface Magnetic Particles have a thick layer of polymer coating on the surface of the particles to fully encapsulate the iron oxide coating. There is no exposed iron oxide on the surface of the particles.

Cylindrical Neodymium magnets (Bunting Magnetics Co) are moved along the length of the capillary. The magnets are located around the capillary to mix the particles, Magnets of grade N35 and N40 were used for all experiments.

Teflon tubes were found to be better than glass tubes and were used for all experiments. The particles stick to the glass more than Teflon. It is hypothesized that
Teflon, being more hydrophobic than glass, repels the hydrophilic particles more than glass which is hydrophilic because of the presence of the carboxyl group on the particle surface. However, the particles do not stick to Teflon on because it is extremely hydrophobic.

Fluorescent reading is not taken in the tube for the following experiments, although it is possible to attach an optical system to the capillary system. After completion of the chemical reaction, the particles are taken out of the tube and read in a flow cytometer, All readings are standardized with respect to the SPHERO Rainbow Calibration Particles, The SPHERO Rainbow Calibration Particles contain a mixture of several similar size particles with different fluorescence intensities. Every particle contains a mixture of fluorophores that allows excitation at any wavelength from 365 to 650 nm. This enables the calibration of all channels in the flow cytometer with the same set of particles. The fluorophores used are very stable but non-spectral matching to commonly used fluorophores such as FITC, PE or PE-Cy5. Dilution of a few drops of the particles flam the chopper bottle to 1 mL of a diluent provides adequate particle concentration for flow cytometer calibration. The diluted Rainbow Calibration Particles remain stable following repeat freezing and thawing.

Strepatividin-Biotin Reaction in a Tubular Processor and a Microfuge Tube

A tubular processor for use as a diagnostic device preferably is able to carry out an assay without loss in sensitivity. Moving the particles through oil could denature the proteins bound to the particle or form a layer on the particle making diffusion from the bulk solution to the particle surface difficult.

A streptavidin-biotin system was utilized. The biotin-avidin or biotin-streptavidin interaction has some unique characteristics that make it beneficial as a general bridge system. Avidin, streptavidin, and NeutrAvidin biotin-binding protein each bind four biotins per protein molecule with high affinity and selectivity.

Unlabeled Streptavidin coated SPHERO Smooth Surface Magnetic Particles (1% w/v) with an average diameter of 3µ were used for the experiment. In each of the following experiments, $0.7*10^6$ magnetic particles were used. The particles were washed in Phosphate Buffer Saline (PBS), magnetically separated and resuspended in 60 µL of PBS buffer containing 0.1% Nonidet P-40 detergent. Different concentrations of Alexa-488-Biotin were dissolved in Na-Phosphate buffer containing 0.1% Nonidet P-40

The following solutions were injected into the capillary in the sequence given, each separated by 60 µL of silicone oil:
(a) 60 µL of PBS buffer containing the magnetic particles
(b) 60 µL wash buffer of PBS containing 0.1% Nonidet P-40
(e) 200 µL Na-Phosphate buffer containing a known concentration of Alexa-488-Biotin and 0.1% Nonidet P-40
(d) 60 µL wash buffer of PBS containing 0.1% Nonidet P-40

The particles were first moved magnetically from 'solution-a' to the chamber containing the wash buffer (solution-b). This cleans the particles of debris. They were then moved to the chamber containing the Alexa-488-Biotin allowing the Streptavidin coated particles to bind to Alexa-488Biotin (solution-c). The particles were constantly mixed magnetically. The reaction was allowed to continue for 90 minutes and then the particles were moved to the next chamber (solution-d) to wash off any debris which might have stuck to the particles. Moving the particles from one chamber to the next through the silicone oil involves the particles coming together into a clump so that they can cross the oil-water barrier. Hence, each time the particles move across from one chamber to the next, they are made to mix well by moving the magnets. The particles are then collected and fluorescence on the particle is measured in a flow cytometer.

The Alexa Fluor dyes used for the experiment are a series of superior fluorescent dyes that span the near-UV, visible, and near-IR spectra. These dyes, without exception, produce brighter conjugates compared to fluorescein. The Alexa-488 absorbs light at 495 nm, emits at 519 nm and has an extinction coefficient of 71000. The dye is water soluble and remains highly fluorescent over a broad pH range.

An identical reaction was carried out in a microfuge tube. $0.7*10^6$ particles were washed in PBS, magnetically separated and resuspended in 60 µL of PBS buffer containing 0.1% Nonidet P-40 detergent. The particles were then mixed with the following solutions each time being magnetically separated before being resuspended in the next solution.
(a) 60 µl of PBS buffer containing the magnetic particles
(b) 60 µL wash buffer of PBS containing 0.1% Nonidet P-40
(c) 200 µL Na-Phosphate buffer containing a known concentration of Alexa-488-Biotin and 0.1% Nonidet P-40
(d) 60 µL wash buffer of PBS containing 0.1% Nonidet P-40

As was the case of the reaction in the capillary, the Streptavidin coated magnetic particles were allowed to mix with biotin containing buffer for 90 minutes. The particles were mixed constantly during this time. Fluorescence readings were taken from these particles and compared with the fluorescence readings of the particles from the capillary system.

Figure 8:
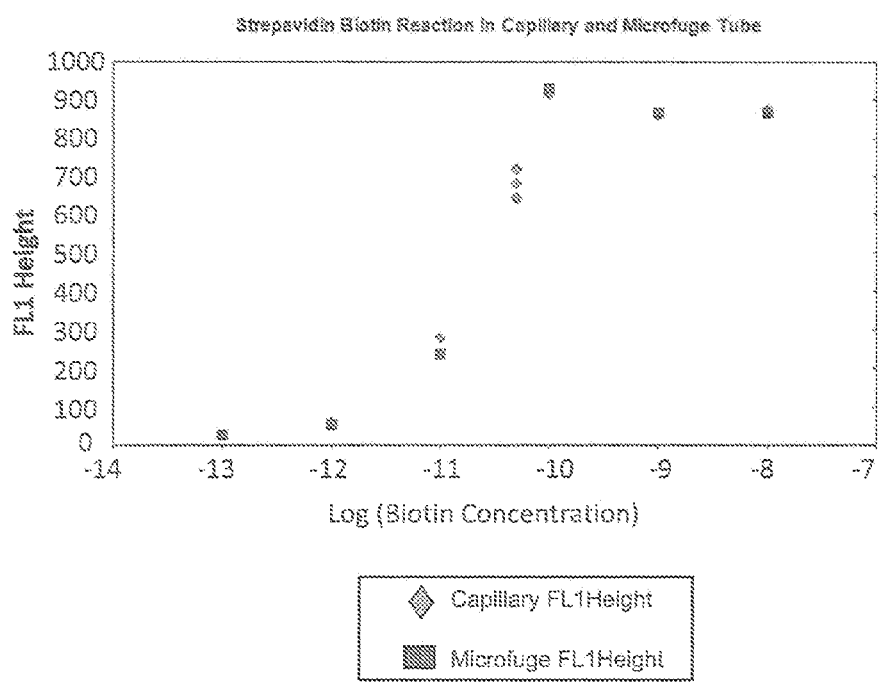
FIG. 8 shows a plot of FL1 height verses Log (Biotin concentration).

FIG. 8 shows the value of FL1 Height measured in a flow cytometer at different concentrations of Biotin. The diamonds represent the signal for a Streptavidin biotin reaction carried out in the capillary system whereas the pink squares represent the signal for a Streptavidin biotin reaction carried out in the microfuge rube. All measurements were standardized by keeping the third peak of the rainbow at a fixed value. As can be seen from the plot, the particles are completely saturated until a Biotin concentration of $10^{-10}$ after which the signal starts reducing. The amount of biotin which binds on to the Streptavidin coated particles is similar irrespective of whether the reaction is carried out in a capillary or a microfuge tube. The difference between the two reactions is not statistically significant at all measured concentrations of biotin. The graph shows that there is some quenching in the fluorescent signal at high concentrations of biotin. FIG. 8 shows 5 replicates for the Streptavidin-biotin reaction in a tubular processor at a biotin concentration of $0.5*10^{-10}$ M. This represents the variability of the reaction from one run to another.

Figure 9:
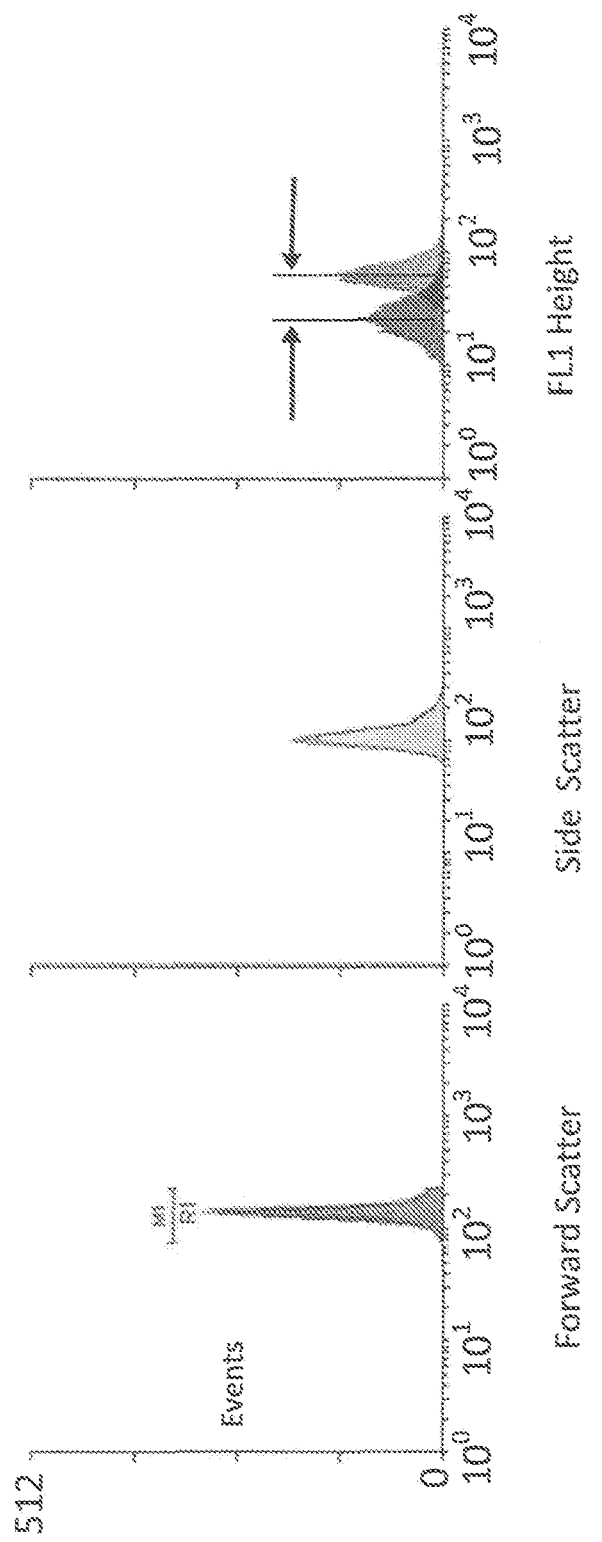
FIG. 9 shows a plot of events recorded by the flow cytometer verses forward scatter, side scatter and FL1 height.

The procedure followed for the experiment is the same as the previous experiment described above. FIG. 9 consists of two superimposed images measured for two sets of particles, namely:
(a) Streptavidin coated SPHERO Smooth Surface Magnetic Particles reacting with $10^{-12}$M Biotin solution
(b) Streptavidin coated SPHERO Smooth Surface Magnetic Particles reacting with deionized water The forward scatter and the side scatter is the same for the two sets of particles, as would be expected because of identical size and surface roughness of the two sets of particles. The FL1 height, which is a measure of the amount of fluorescence emitted off the particle surface and thereby a direct measure of the amount of biotin bound to Streptavidin is different for the two sets of particles. FIG. 9 shows that the median FL1 height (peak) when the particles reacts with $10^{-12}$ M Biotin is distinctly distinguishable and greater than the median height when the Streptavidin coated particles react with water. The sensitivity of the device was found to be $10^{12}$M for biotin (more than 2 dB above the blank).

Particle Transport Between Tubes

Figure 10:
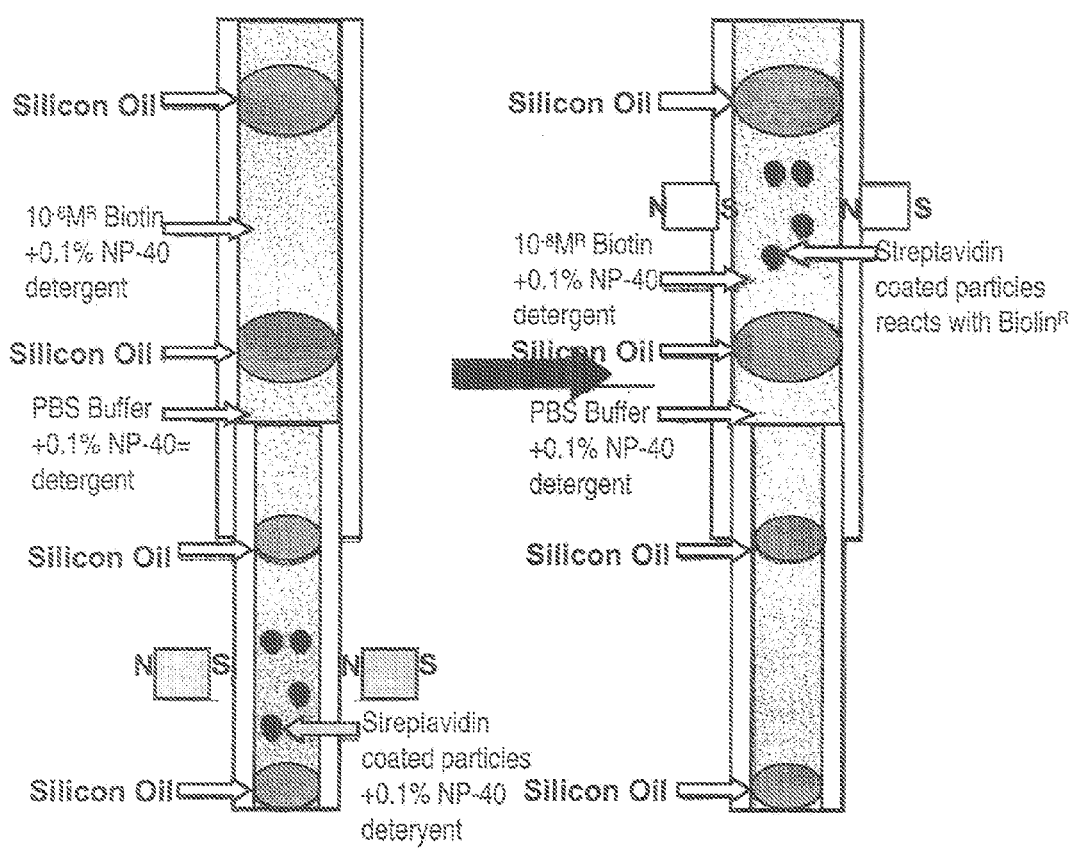
FIG. 10 shows an illustration of the movement of streptavidin coated magnetic particles from one capillary to another followed by reaction with biotin.

As shown in FIG. 10, one tube is inserted into another such that the outer diameter of the thinner tube is almost equal to the inner diameter of the larger tube. Streptavidin coated particles are moved to the chamber containing PBS buffer. While doing so, it also moves from one capillary to another. It is then moved to a chamber containing PBS buffer containing $10^{-8}$M Alexa-488-Biotin and 0.1% Nonidet-P40 (NP-40). Moving from one chamber to another involves crossing regions of silicone oil. The particles were allowed to react with Alexa-488-biotin for 90 minutes, after which the particles are taken out and their fluorescence measured in a flow cytometer. The fluorescent readings indicate that the reaction occurs in spite of moving from one capillary to another.

In a portable diagnostic device, the reagents might be potentially present in one tube while the sample to be measured may be collected in another a separate tube or vessel suitable for collection of sample. This experiment demonstrated the feasibility of allowing the particles to react with the sample in a tube or collection vessel and then moving them to another tube where the remaining reagents are present, thereby allowing the proceeding reactions to be carried out.

Effect of Silicone Oil

One of the factors that affects the diagnostic device is the effect of the silicone oil on the particles. It was investigated if the oil sticks to the particle during the movement of the particle through the oil region. For this purpose, a fluorescent dye, pyromethene 546, was dissolved in silicone oil. Pyromethene is an oil soluble laser dye which fluoresces at 546 nm. The particles were made to move through a region of silicone oil containing pyromethene 546. The particles were then taken out of the capillary and the fluorescence signal was measured in a flow cytometer (FIG. 11a).

In another experiment, the particles were moved through silicone oil containing pyromethene 546 and then mixed in PBS buffer containing 0.1% Nonidet P40. A magnet was used to agitate these particles. The particles were then taken out of the capillary and the fluorescence signal measured in a flow cytometer as shown in FIG. 11b.

The forward scatter value depicts the size of the particle while the side scatter gives information about the surface property of the particle. In FIG. 11a, the forward scatter plot shows a broad distribution although the particles are about the same size. This demonstrates that the oil is sticking to the particle or droplets of oil of various sizes are formed. Upon agitating the particles in PBS buffer after moving the particles through oil, the particle size distribution shows two distinct peaks as expected, namely the particles and the doublets of the particles (FIG. 11b). The side scatter plot in FIG. 11a also shows two peaks suggesting that there might be little droplets of oil formed as well. The FL1 median value of FIG. 11a is 73 which demonstrates that some of the fluorescent dye has migrated with the particles. This can be washed away by mixing the particles and therefore a lower fluorescence value 38 is obtained in FIG. 11b.

Example 4

Efficiency of Commercial Viral RNA Purification Using Liquid Wax

This example demonstrates that a purification method that transports RNA bound to paramagnetic particles through a liquid wax medium is adaptable to commercially-available kits which employ different types of particles and a variety of lysis, wash, and elution buffers. The kits tested contained silica (Ambion), iron oxide (Abbott/Promega) and cellulose (Cortex) magnetic particles. In addition to differences in particle chemistry, these kits vary in the composition of their respective lysis and elution buffers as well as the intermediate wash buffers.

Viral particles spiked into normal plasma were purified according to the kit manufacturers' instructions, including all of the wash steps between lysis and elution, and determined the levels of RNA by real time PCR. Spiked plasmas were then purified with the wax phase method using only the lysis and elution buffers and compared levels of RNA.

Comparison of RNA concentrations, expressed in Ct units, showed that the efficiency of the liquid wax transfer purification methodology is equivalent to that of procedures in manufacturer-specified guidelines. Taken together, these results indicate that the exclusion of the lysis buffer by liquid wax is an appropriate replacement for the multiple manual washes typically prescribed by RNA purification systems.

Wax-Bridge Cuvette

Figure 12:
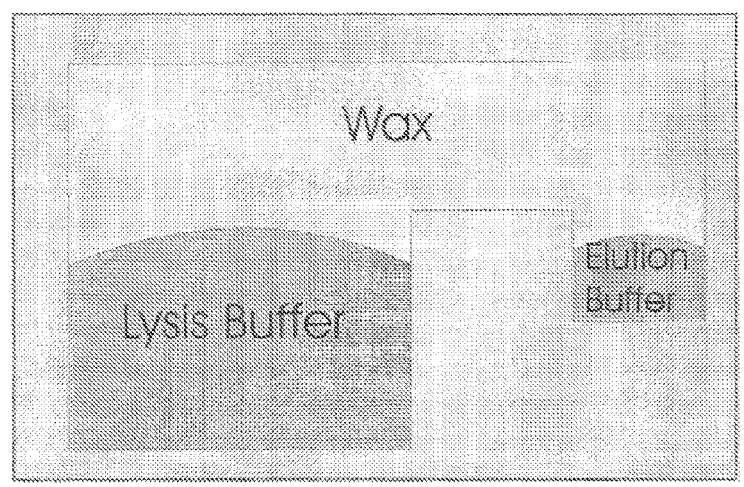
FIG. 12 shows a schematic of a two-chamber cuvette used in some embodiments of the present invention.
Figure 13:
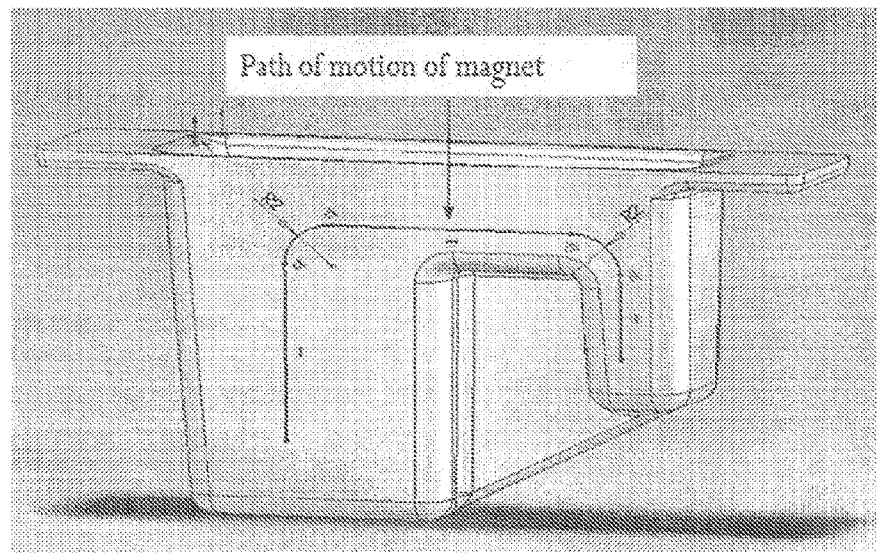
FIG. 13 shows a schematic of a two-chamber cuvette used in some embodiments of the present invention.

All experiments were performed in a two-chamber cuvette shown in FIGS. 12 and 13, which were designed to facilitate moving particles from the lysis buffer to the elution buffer. As shown in FIG. 12, lysis buffer is added to the chamber on the left, and elution buffer is added to the chamber on the right. Liquid wax is then added which covers both buffer solutions and forms a bridge between the two chambers. When a magnet is placed on the side wall of the lysis chamber, particles are drawn to the wall forming a pellet. As shown in FIG. 13, the magnet is then moved up dragging the pellet along the wall through the lysis buffer into the oil layer. The magnet is then moved laterally dragging the particles through the oil bridge until the pellet is above the elution chamber. Finally, the magnet is moved down dragging the particles out of the oil into the elution buffer.

Manufacturers' Protocols

The Ambion MagMax Viral RNA Isolation Kit (Catalog No. AM1929), Abbott/Promega M Sample Preparation System (Catalog No. 02K02-24), and Cortex Biochem Maga-Zorb® RNA Isolation Kit (Catalog No. MB2001) were tested. Viral RNA samples were processed with each manufacturers reagents following the kit protocols, which include multiple washing steps.

Liquid Wax Protocols
Ambion MagMax Viral RNA Reagents:
Sample Lysis

25 μL of plasma containing $1.5 \times 10^6$ cp/mL HIV-1 virions was added to 802 μL of Lysis buffer (composition: 400 μL manufacturer-supplied Lysis/Binding concentrate, 400 μL absolute isopropanol, 2 μL manufacturer-supplied carrier RNA) in 1.5 mL screw-cap tubes and mixed by pipet. Lysis proceeds for up to 10 minutes at 50° C., in the presence of 20 μL well-suspended magnetic particles (manufacturer-supplied; composition: 10 μL particles, 10 μL Binding Enhancer). Particles may be added following the initial lysis step or be present during lysis; no discernable effect on purification efficiency has been observed.

Cartridge Setup

Magnetic particles are sedimented on a magnetic rack and 600 μL of supernatant liquid is discarded to permit loading into a prepared cartridge. Up to 250 μL of the slurry containing lysis buffer and RNA-bound particles is transferred to the 'lysis' chamber of the cartridge. 25 μL of a manufacturer-supplied Tris-EDTA elution buffer is loaded into the 'elution' chamber of the cartridge. Chili-Out Liquid Wax (Bio-Rad) is layered on top of the fluid in both chambers such that a wax 'bridge' is formed across the top of the cartridge, typically requiring 800 μL of liquid wax. Cartridges for multiple samples may be prepared in batch in this manner and arrayed on a fabricated rack.

Purification

RNA-bound heads are accumulated into a tight pellet by a magnet. Cartridges are handled individually for the transfer of particles from lysis' to 'elution' chambers. Magnetic particles are transferred through the wax and into the elution buffer by magnet in a steady manner such that the beads remain in a tight pellet and carryover of lysis buffer is minimized. Once in the elution buffer, the beads are mixed by manual manipulation of the magnet.

Sample Recovery

Liquid wax is aspirated from the cartridge such that a minimal amount (1 mm at meniscus) remains over the 'elution' chamber without sample loss. The cartridge is set for 4 minutes at −20° C. such that the liquid wax solidifies but the elution buffer/bead slurry remains in liquid phase. The liquid wax plug can be removed by pipet tip or pierced for extraction of elution buffer. The elution buffer/bead slurry is transferred to a 1.5 mL screw-cap tube and heated for up to 10 minutes at 70° C. to facilitate complete elution of viral RNA into the supernatant buffer. Beads are sedimented on a magnetic rack and up to 50 μL of RNA in Tris-EDTA buffer is collected from each tube, ready to use for qRT-PCR.

Abbott/Promega Reagents:

Sample Lysis

25 μL of plasma containing $1.5 \times 10^6$ cp/mL HIV-1 virions was added to 600 μL of Lysis buffer (supplemented with 2 μL manufacturer-supplied carrier RNA) and 25 μL iron-oxide magnetic particles in 1.5 mL screw-cap tubes and mixed by pipet. Lysis proceeds for up to 10 minutes at 50° C.

Cartridge Setup

After lysis, magnetic particles were sedimented and 400 μL of supernatant was discarded, 25 μL of a high-salt elution buffer is added to the 'elution' chamber. Up to 250 μL of the slurry containing lysis buffer and RNA-bound particles is transferred to the lysis' chamber of the cartridge. Chill-Out Liquid Wax (Bio-Rad) is layered on top of the fluid in both chambers such that a wax 'bridge' is formed across the top of the cartridge, typically requiring 800 μL of liquid wax. Cartridges for multiple samples may be prepared in batch in this manner and arrayed on a fabricated rack.

Purification and Sample Recovery

A procedure identical to that employed for the Ambion kit was used,

Cortex Biochem Reagents:

Sample Lysis

25 μL of plasma containing $1.5 \times 10^6$ cp/mL, HIV-1 virions was treated with 20 μL Protease K by gentle mixing in a 1.5 mL screw-cap tube, 200 μL of manufacturer-supplied Lysis buffer was added and the sample mixed by pulse-vortexing for 15 seconds, followed by heating up to 15 minutes at 55° C. 500 μL of manufacturer-supplied Binding buffer and 20 μL of monodisperse MagaZorb Reagent was added to the sample and incubated 10 minutes at room temperature (20° C.) with occasional mixing by inversion.

Cartridge Setup

Magnetic particles are sedimented on a magnetic rack and 500 μL of supernatant liquid is discarded to permit loading into a prepared cartridge. Up to 250 pt of the slurry containing lysis buffer and RNA-bound particles is transferred to the 'lysis' chamber of the cartridge. 25 μL of a manufacturer-supplied Tris-EDTA buffer was added to the 'elution' chamber. Chill-Out Liquid Wax (Bio-Rad) is layered on top of the fluid in both chambers such that a wax 'bridge' is formed across the top of the cartridge, typically requiring 800 μL of liquid wax. Cartridges for multiple samples may be prepared in batch in this manner and arrayed on a fabricated rack.

Purification and Sample Recovery

A procedure identical to that employed for the Ambion kit was used, with the exception that the elution buffer/bead slurry was heated to 70° C. for 15 minutes to facilitate elution of viral RNA.

Comparison of Procedures

The adaptability of various viral RNA purification chemistries to the liquid wax purification method was evaluated by qRT-PCR using reagents supplied with the Abbott m2000rt assay kit. In each case, HIV-1 virion containing plasma was used as template for qRT-PCR analysis and was complemented by appropriate positive (pure HIV-1 transcript) and negative (mock plasma purification or water) controls. All purification samples include carrier RNA as an internal control and were performed in replicate. From each RNA preparation, 5 μL RNA was used for analysis, yielding 7,500 copies of HIV-1 RNA in each reaction. A qRT-PCR mixture for a single sample is described in Table 4 below:

TABLE 4

| Component | Volume (μL) |
| --- | --- |
| m2000rt oligo. pre-mix | 8.75 |
| Tth polymerase (Roche) | 0.75 |
| Manganese acetate (Roche) | 2.5 |
| Crowding reagents (5X) | 5.0 |
| Purified RNA | 5.0 |
| Nuclease-free dH$_2$O | 3.0 |

Results of qRT-PCR Analysis

Ct values given by the qRT-PCR instrumentation are Oven in Table 5 below:

TABLE 5

| Magnetic particle type | Liquid Wax Mean Ct | Multi-step Wash Mean Ct |
| --- | --- | --- |
| Silica (Ambion) | 20.69 | 18.69 |
| Iron oxide (Abbott/Promega) | 21.86 | 19.00 |
| Cellulose (Cortex Biochem) | 20.32 | 19.83 |

For a set number of HIV-1 template copies, there was little variance observed in the reported Ct values from qRT-PCR analysis between chemistries tested and purification method employed. Negative amplification and mock purification controls in these experiments gave no or negligible Ct values in these experiments. The phase gate purification procedure is comparable in efficiency to kit manufacturer protocols, demonstrating that the liquid wax exclusion of lysis buffer and other PCR inhibitors is as effective as multiple washing. Spectrophotometry of eluted RNA samples from the Abbott/Promega samples shows no absorbance at 230 nm. Guanidinium is present in high molar concentrations in this lysis buffer and absorbs ultraviolet light at 230 nm; the absence of an absorbance peak shows that the carryover of this contaminant is low. That the observed Ct values are consistent across replicates, largely invariant amongst purification chemistries and comparable between purification methodologies demonstrates that good RNA recovery has been achieved.

Example 5

Isolation of CD4+ T-Cells

Fresh Peripheral Blood Mono-Nuclear Cells (PBMNC's) were purchased from Allcells (Emeryville, Calif.). Dynabeads CD4 magnetic particles (4.5 um diameter), coated with anti-CD4 antibody were purchased from Invitrogen (Carlsbad, Calif.).

1.2 ml of PBMNC's were mixed with 50 µl of the Dynabeads CD4 magnetic particles. The capture reaction was allowed to go for 45 minutes at 4° C.; with gentle tilting and rotation. The CD4+ve T-Cell positive isolation was compared using three procedures.

a) Positive isolation using Dynabeads CD4 protocol: 200 µl of the above stock was aliquoted into the Well 1 of the research cartridge (shown in FIG. 12, labeled lysis buffer, and FIG. 13). A magnet was placed on the side of the cartridge for 1 minute, causing the magnetic particles and captured cells to form a pellet on the side. The supernatant was aspirated and discarded. The pellet was washed 3 times by re-suspending, in 200 µl PBS and separating using a magnet. After the final wash, 60 µl of 0.2% Triton X-100 was added to lyse the cells.

b) Positive extraction through Chill-Out Liquid Wax (Bio-Rad, Hercules, Calif.). 200 µl of the stock solution was aliquoted into Well 1 of the research cartridge. 60 µl of 0.2% Triton X-100 lysis buffer was aliquoted into Well 2 of the research cartridge (shown in FIG. 12, labeled elution buffer, and FIG. 13) which was separated from Well 1 by Chill-Out Liquid Wax. A magnet was placed on the side of the cartridge for 1 minute, drawing the magnetic particles and captured cells onto the side of Well 1. The pellet was then slowly moved through the wax into Well 2 by dragging the magnet along the path shown in FIG. 13. The magnet was used to agitate the particles in Well 2.

c) Positive extraction through canola oil (Jewel-Osco/Supervalu, Eden Prairie, Minn.). 200 µl of the stock solution was aliquoted into Well 1 of the cartridge. 60 µl of 0.2% Triton X-100 lysis buffer was aliquoted into the lysis chamber which was separated from Well 2 by canola oil. A magnet was placed on the side of the cartridge for 1 minute, drawing the magnetic particles and captured cells onto the side of Well 1. The pellet was then slowly moved with a magnet through the canola oil into Well 2. The magnet was used to agitate the particles in Well 2.

The efficiency of the transfer through the lipophilic barriers was determined by measuring the amount of cellular DNA in an aliquot of the solution in Well 2 with a real-time PCR assay for the β2-microglobulin gene. In each of the experiments, the particles were drawn to the side of Well 2 with a magnet; and 60 ul of the lysed cell suspension was transferred into Eppendorf tubes. 5 ul of each sample was then obtained and used for RT-PCR using the Phusion GC assay for β2-microglobulin (New England Biolabs, Ipswich, Mass.), Results Table 6 below shows the number of cycles required to reach the threshold fluorescence intensity of the real time PCR assay:

TABLE 6

| Cell purification | Ct value |
| --- | --- |
| DynalBeads protocol | 27.59 |
| Chill-Out Wax | 27.14 |
| Vegetable Oil | 28.99 |

The results show that the Ct values obtained from the three cell isolation procedures w comparable. Since the assay quantified β2-microglobulin, the results show that the genetic material in the cells was preserved while being moved through the wax and oil.

Example 6

RNA Purification from Plasma Using Dextran PMPs

In order to eliminate all wash steps for purifying nucleic acids and to eliminate all contact between the processing system and the sample, PMPs were transported between wells using an externally applied magnetic field. The wells are connected with a hydrophobic liquid through which PMPs are transported (FIG. 12). The hydrophobic liquid acts as a barrier between the lysis chamber and the elution chamber, preventing mixing of the two solutions. Upon application of the magnetic force, the PMPs are moved through the hydrophobic liquid, transporting NAs from the lysis chamber to the elution chamber while the lysis and elution buffers remain stationary. The hydrophobic liquid acts as an immiscible phase filter (IPF), which reduces processing to only three steps: cell lysis/NA binding, PMP transport, and NA elution. To demonstrate the feasibility of incorporating IPF into a RNA purification protocol, HIV-1 RNA was extracted from plasma as is done in measuring viral load. Quantitative measurement of HIV-1 is important for monitoring disease progression and evaluating antiretroviral drug therapy outcome (Mylonakis, Paliou et al., Am. Fam. Phisician 63(3) 483 2001). Since viral load measurement is technically demanding due to the relatively low viral copy number and abundance of PCR inhibitors in samples derived from human blood (Dineva, Mahilum-Tapay et al. *Analyst* 132: 1193-1199 2007), this assay provides a good model system.

HIV-1 virus, acquired from Rush Virology Quality Assurance Laboratory at $1.5 \times 10^5$ copies/ml of plasma, was diluted in seronegative plasma to obtain HIV-1 concentrations of 300, 60 and 12 copies/a respectively. The Ambion MagMax™ Total RNA isolation kit (Applied Biosystem; Foster City, Calif.) manual protocol was performed as per manufacturer's recommendations. For purification with the IPF method, lysis and binding reagents constituting of 200 µL of Ambion Lysis/Binding solution concentrate (Applied Biosystem; Foster City, Calif.), 200 µl, of isopropyl alcohol, 1 µL of carrier RNA (Applied Biosystem; Foster City, Calif.), 5 µL of Ambion PMPs and 5 µL of Binding Enhancer (Applied Biosystem; Foster City, Calif.) were added to the larger chamber of the cartridge and mixed. 50 µL of plasma containing HIV-1 virus was then added to it and mixed for 4 minutes using the automated system. 50 µL of elution buffer was aliquoted into the smaller chamber of the IPF cartridge and the two aqueous fluids were overlaid with Chillout™ liquid wax (Biorad Laboratories; Hercules, Calif.) as shown in FIG. 12. An automated system aggregated the PMPs for 2 minutes using the external magnet and moved the aggregate from the lysis buffer to the elution buffer. The elution buffer containing the PMPs was heated to 55° C. for 10 minutes to elute the RNA. The PMPs were aggregated and removed from the elution buffer. HIV-1 viral load quantification was performed using the Abbott RealTime HIV-1 Amplification Reagent Kit (Huang, Salituro et al. 2007) (Abbott Molecular, Des Plaines, Ill.) in 25 µl reaction volumes with the addition of 0.2 mg/ml bovine serum albumin (B8667. Sigma), 150 mM trehalose (T9531; Sigma) and 0.2% Tween 20 (28320; Pierce Thermo Fisher Scientific) and 5 µl template. Amplification reactions were performed in Cepheid SmartCycler II (Sunnyvale, Calif.).

Figure 14:
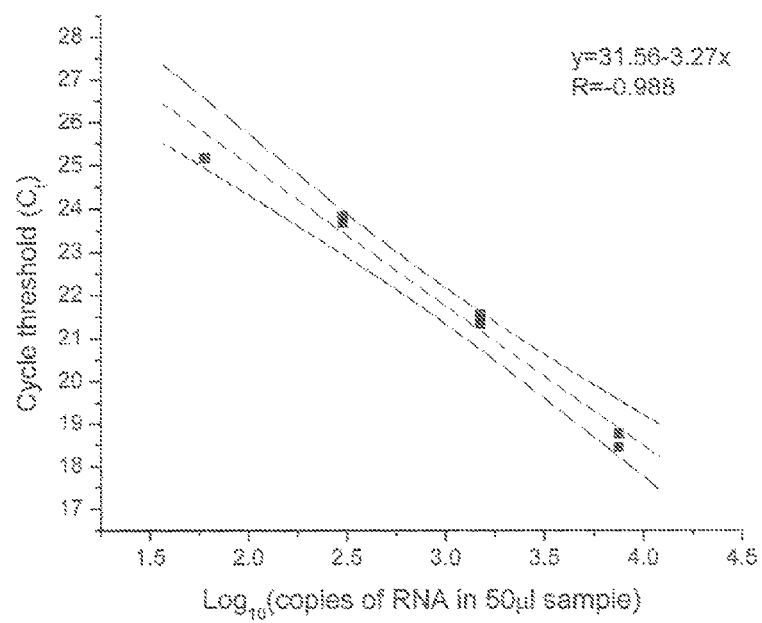
FIG. 14 shows qRT-PCR for HIV-1 from plasma using an immiscible phase filter (IPF) method: Standard curve of $C_t$ values far 4 different RNA concentrations run in duplicate plotted verses the $\log_{10}$ of the HIV-1 viral copy number.
Figure 15:
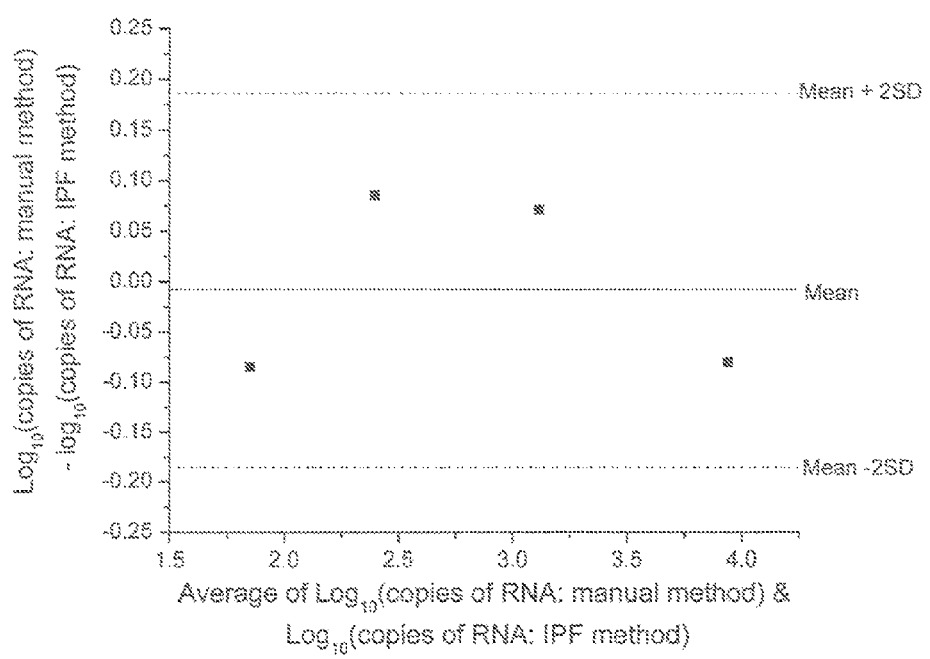
FIG. 15 shows a Bland-Altman plot comparing the IPF and manual method of purification: Solid black squares show difference between the two methods, solid line ($y=-0.00772$) plots the mean difference between the two methods and the dashes lines show the mean $+2$ and $-2$ standard deviations (SD) of the mean.

The purified RNA was amplified using the Abbott Real-Time HIV-1 Amplification Kit. A PCR efficiency of E=102% was observed (FIG. 14), indicating that the inhibitor carryover is minimal even after eliminating the four wash steps and the alcohol evaporation step required for the standard protocol. Comparing the IPF and the standard protocol for RNA purification using the Ambion MagMax™ Total RNA isolation kit showed that at 0.05 level of significance ($\alpha$=0.05), there was no statistical difference between the two methods (p-value-0.967) (FIG. 15). Ten replicates each at several low copy numbers were purified and it was found that 60 copies of viral RNA could be detected in the PCR reaction with 100% sensitivity. Because 50 µl of plasma were used, this corresponds to 600 copies per ml of blood with 100% sensitivity.

Example 7

Purification of *Chlamydia* and Gonorrhea DNA from Urine

In order to eliminate all wash steps for purifying nucleic acids and to eliminate all contact between the processing system and the sample, PMPs were transported between wells using an externally applied magnetic field. The wells are connected with a hydrophobic liquid through which PMPs are transported (FIG. 12). The hydrophobic liquid acts as a barrier between the lysis chamber and the elution chamber, preventing mixing of the two solutions. Upon application of the magnetic force, the PMPs are moved through the hydrophobic liquid, transporting NAs from the lysis chamber to the elution chamber while the lysis and elution buffers remain stationary. The hydrophobic liquid acts as an immiscible phase filter (IPF), which reduces processing to only three steps: cell lysis/NA binding, PMP transport, and NA elution. To demonstrate the feasibility of using the IPF method to extract NA from urine, bacterial DNA was purified from *Chlamydia trachomatis* (CT) and *Neisseria gonorrhoeae* (NG) for diagnosis of these sexually transmitted diseases.

The urine samples were prepared by combining *Chlamydia: ATCC trachomatis* serotype F in McCoy cell culture suspension and lyophilized *Neisseria gonorrhoeae* resuspended in PBS containing 30% glycerol with control urine (Fisher Scientific, PA). The manual protocol was carried out using the Abbott RealTime CT/NG assay as per the manufacturer's protocols. For purification with IPF method, 200 µL of Ambion Lysis/Binding solution concentrate (Applied Biosystem; Foster City, Calif.), 200 µL of isopropyl alcohol, 1 µL of carrier RNA (Applied Biosystem; Foster City, Calif.), 5 µL of Ambion PMPs and 54, of Binding Enhancer (Applied Biosystem; Foster City, Calif.) were mixed. 200 µL of urine sample was then added to it. The solution was heated to 55° C. for 10 minutes and the two-step purification was carried out as with the plasma samples. As described previously (Marshall et al., J. Clin. Microbiol., 45:747-51, 2007), the purified DNA was amplified using the Abbott RealTime CT/NG assay in a 50 µL reaction volume. Amplification reactions were performed in the Abbott Molecular m2000rt instrument (Abbott Park, Ill.).

Figure 16:
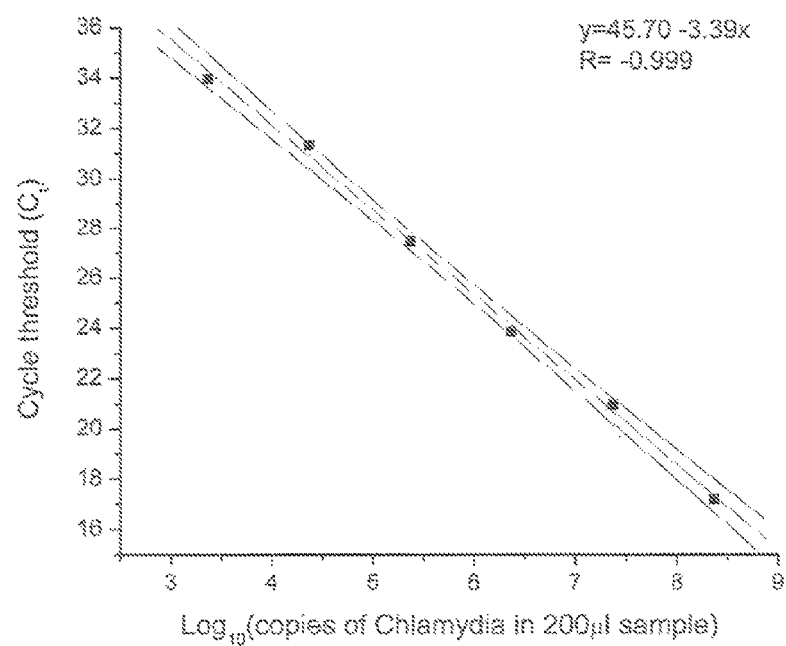
FIG. 16 shows IPF quantification by qPCR of *Chlamydia* from urine samples.
Figure 17:
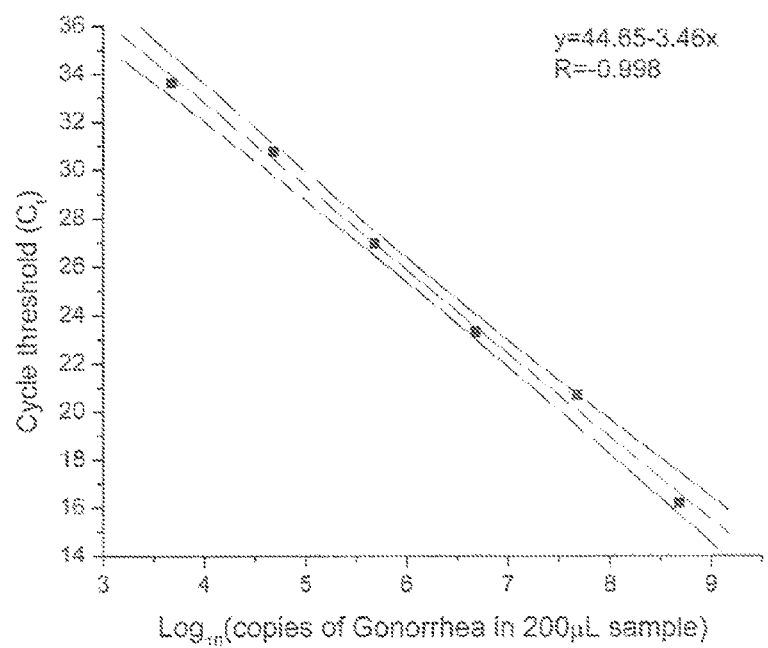
FIG. 17 shows IPF quantification by qPCR of gonorrhea from urine samples.
Figure 18:
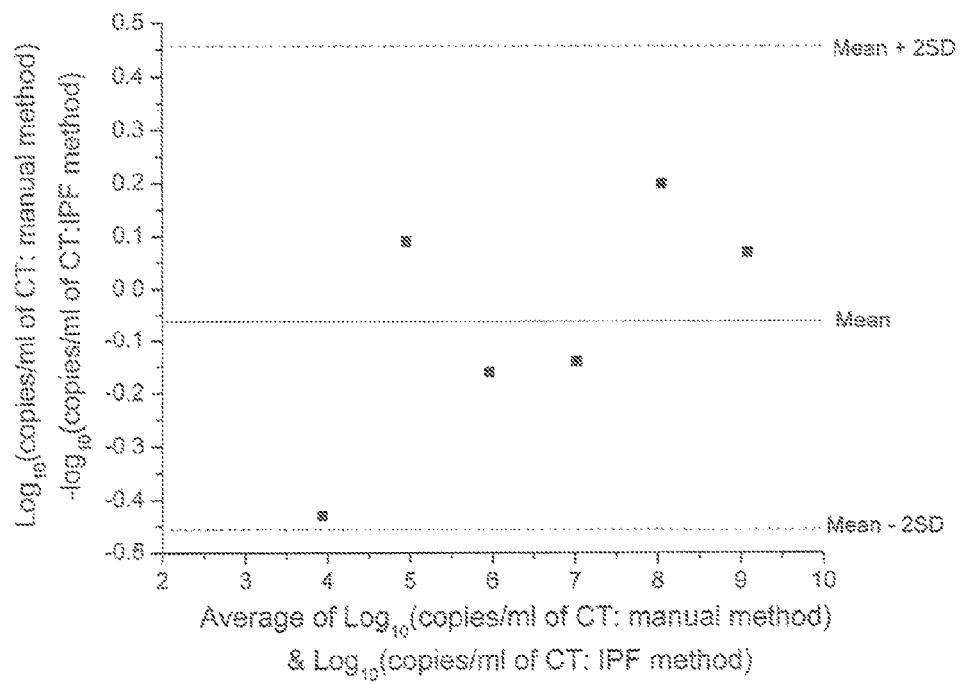
FIG. 18 shows Bland-Altman plot comparing the IPF and manual method of purification of *Chlamydia*.
Figure 19:
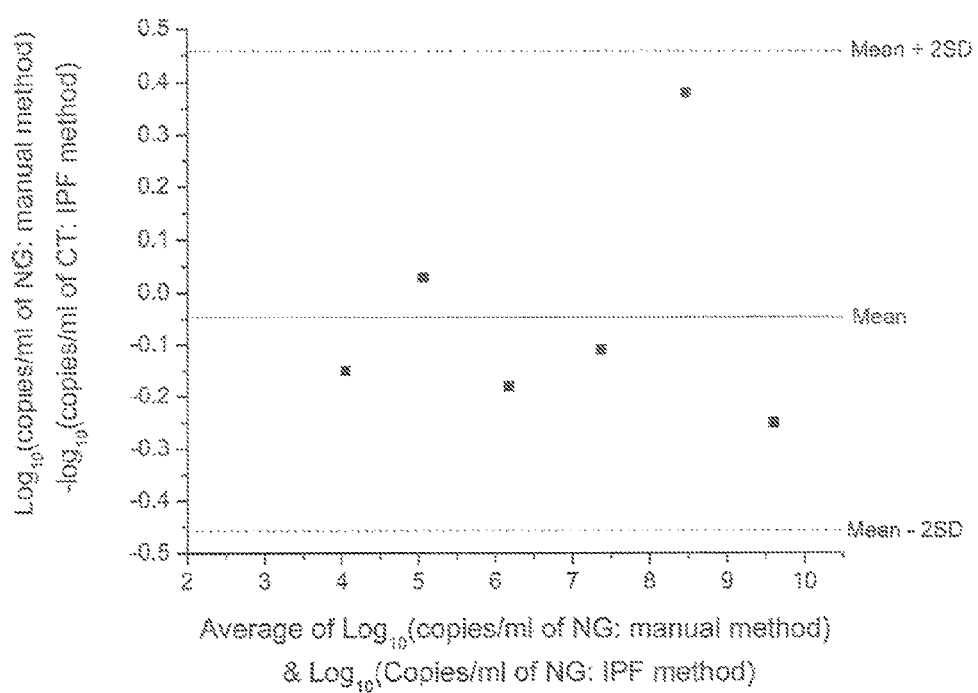
FIG. 19 shows a Bland-Altman plot comparing the IPF and manual method of purification of gonorrhea.

The PCR efficiency for the CT and NG assay over seven orders of magnitude was 97.2% and 94.5% respectively (FIGS. 16-17) indicating that the inhibitor carryover is minimal. These efficiencies were similar to those obtained from the manual extraction method (87.9% and 87.9%, respectively) using the Abbott Realtime CT/NG kit. The Bland-Altman plots of the CT and NG assays show that there is no statistical difference between the standard method using the Abbott DNA purification kit and the IPF method. (FIG. 18-19). At a 0.05 level of significance ($\alpha$=0.05), the two were found to be identical (p-values of 0.42 and 0.70 respectively).

Example 8

Purification of Genomic DNA from Whole Blood

In order to eliminate all wash steps for purifying nucleic acids and to eliminate all contact between the processing system and the sample, PMPs were transported between wells using an externally applied magnetic field. The wells are connected with a hydrophobic liquid through which PMPs are transported (FIG. 12). The hydrophobic liquid acts as a barrier between the lysis chamber and the elution chamber, preventing mixing of the two solutions. Upon application of the magnetic three, the PMPs are moved through the hydrophobic liquid, transporting NAs from the lysis chamber to the elution chamber while the lysis and elution buffers remain stationary. The hydrophobic liquid acts as an immiscible phase filter (IPF), which reduces processing to only three steps: cell lysis/NA binding, PMP transport, and NA elution.

Whole blood (WB) is a rich source of genomic DNA; however, it is an extremely complex medium containing numerous PCR inhibitors in high concentrations. To determine if the method could process such samples, a qPCR assay was developed to detect proviral HIV-1 DNA integrated into peripheral blood mononuclear cells. Proviral DNA detection is used routinely to diagnose infants with HIV-1 (Read and Committee on Pediatric AIDS *Pediatrics* 120(6): e1547-1562 2007). The Promega Magnesil gDNA purification kit which consists of 10 steps (lysis, 7 washes, drying and elution) was adapted for use with the IPF which involved 3 steps (lysis, PMP transport through liquid wax, and elution).

Cultured 8E5 cells (Folks. Powell et al. *J. Exp. Med.* 164 (1): 280-290 1986) (Rush Virology Quality Assurance Laboratory, Chicago, Ill.) containing a single copy of the HIV-1 genome per cell added to WB from a seronegative donor was used to simulate infant blood for the proviral DNA assay. The cells were thawed, counted using a hemoctyometer, serially diluted in phosphate buffer saline (PBS) and added to WB from a seronegative donor at concentrations of 8000 cells/µl, 1600 cells/µl, 320 cells/µl and 64 cells/µl. The Promega Magnesil gDNA purification protocol was carried out at the manufacturer's recommendations. In the IPF method, 25 µL blood was added to 60 µL lysis buffer, agitated for a minute and incubated for 4 minutes at room temperature, 44 µL of lysis buffer and 6 µL of PMPs was added, agitated for a minute and incubated for 4 minutes. 15 µL of lysis buffer and 200 µL of alcohol wash buffer were added to the solution and the IPF purification was carried out as before. The purified DNA was amplified using the Abbott RealTime HIV-1 Amplification Reagent Kit (Abbott Molecular, Des Plaines, Ill.) (Huang, Salituro et al. 2007) in 25 µl reaction volume. Amplification reactions were performed in Cepheid SmartCycler II (Sunnyvale, Calif.).

Figure 20:
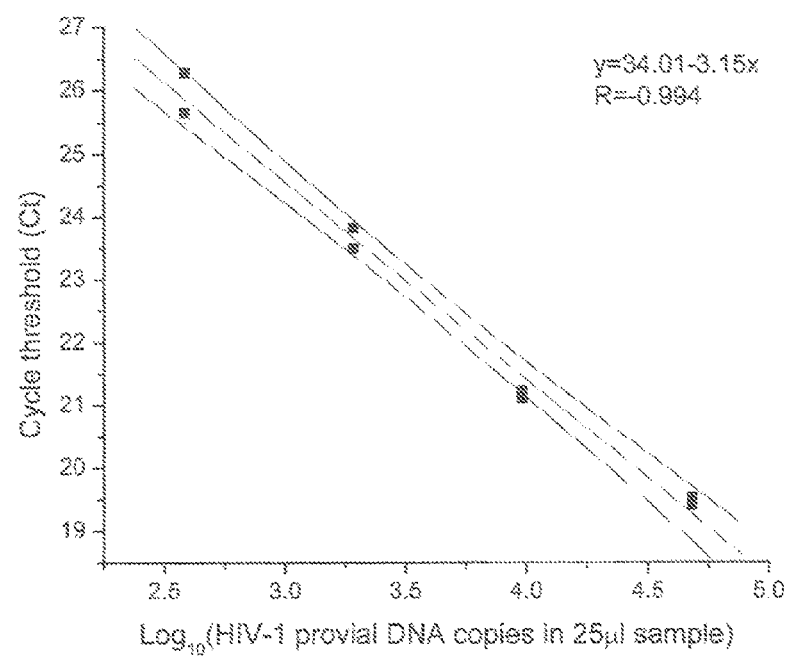
FIG. 20 shows IPF PCR for proviral DNA from 25 μL WB.
Figure 21:
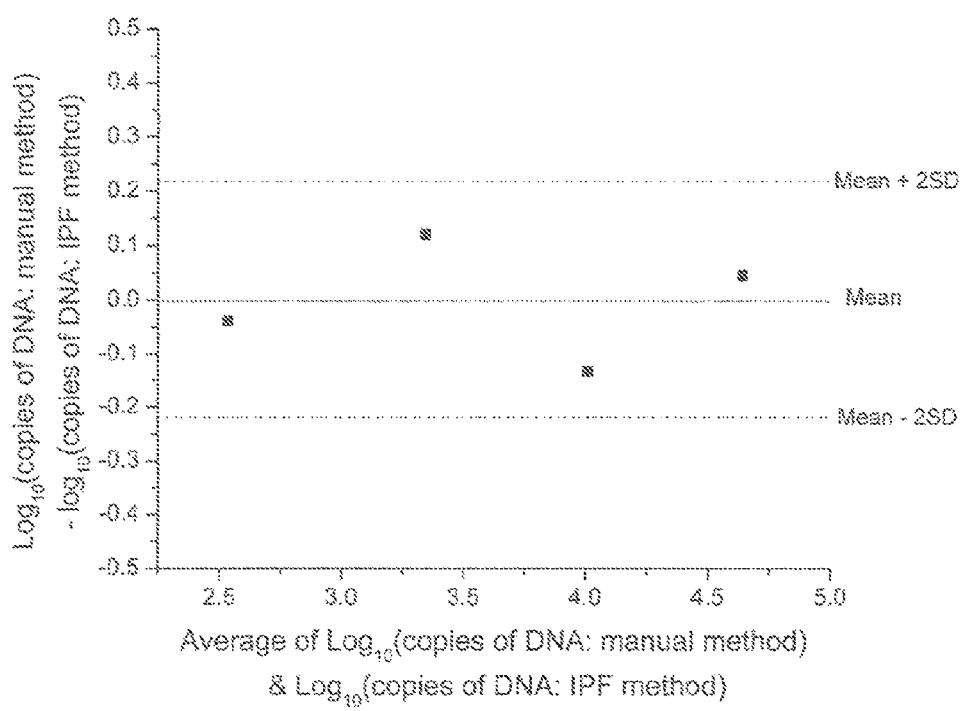
FIG. 21 shows a Bland-Altman plot comparing the IPF and manual method of purification.

Serial dilutions over 4 orders of magnitude yielded a standard curve with a slope of −3.15 and PCR efficiency of 108% (FIG. 20). The Bland-Altman plot of the proviral PCR assays showed that there was no statistical difference between the standard method using the Promega purification kit and the IPF method (FIG. 21). At a 0.05 level of significance ($\alpha$=0.05), the two methods were found to be identical (p-value-0.98).

All publications, patents, patent applications and sequences identified by accession numbers mentioned in the above specification are herein incorporated by reference in their entirety. Although the invention has been described in connection with specific embodiments, it should be understood that the invention as claimed should not be unduly limited to such specific embodiments. Modifications and variations of the described compositions and methods of the invention that do not significantly change the functional features of the compositions and methods described herein are intended to be within the scope of the following claims.

We claim:

1. A method for isolating a material from a sample, comprising:
   placing a sample comprising a material of interest into a first chamber of a device, the first chamber containing a solution comprising water, the device also comprising a second chamber that contains a solution comprising water, and a water immiscible substance disposed between the first and second chambers;
   applying an external, applied force to the material of interest in the first chamber, the applied force capable of interacting with the material of interest or with a component associated with the material of interest; and
   transferring, by relative movement of the applied force with respect to the first chamber, the material of interest from the first chamber, into and through the immiscible substance, and into the second chamber, wherein during said transferring the solutions in the first and second chambers are stationary,
   whereby the material of interest is isolated from the sample.

2. The method of claim 1, wherein placing comprises placing the sample in the first chamber of the device and then depositing the water immiscible substance between the first and second chambers.

3. The method of claim 1, further comprising placing a solid carrier component in a chamber of the device, the carrier component capable of associating with the material of interest.

4. The method of claim 3, wherein said placing comprises placing a solid carrier component comprising a magnetic particles.

5. The method of claim 4, wherein applying an external, applied force comprises applying an external magnetic force.

6. The method of claim 4, wherein transferring comprises transferring the magnetic particles with the material of interest associated with the magnetic particles into and through the water immiscible substance.

7. The method of claim 1, wherein the material of interest is selected from an analyte and a cell.

8. The method of claim 1, wherein transferring comprises moving a sample transport component that generates the force.

9. The method of claim 1, wherein the material of interest is a nucleic acid.

10. The method of claim 9, wherein transferring comprises transferring the nucleic acid from the solution in the first chamber, into and through the water immiscible substance, and directly into the solution in the second chamber.

11. The method of claim 1, wherein placing comprises providing a device wherein a chamber in the device comprises magnetic particles.

12. The method of claim 1, wherein the solution comprising water in the first chamber is a wash solution.

13. The method of claim 1, wherein the solution comprising water in the first chamber is a water-alcohol solution.

14. The method of claim 1, wherein placing the sample in the device wherein the second chamber comprises a reagent selected from the group consisting of an elution medium, an amplification reagent, or both.

15. The method of claim 1, wherein placing comprises placing the sample in the device wherein the first and second chambers are within a plurality of chambers, and the first chamber is preceded by one or more chambers in the plurality of chambers.

16. The method of claim 15, wherein a chamber preceding the first chamber comprises a lysis reagent.

17. The method of claim 16, wherein the chamber comprising the lysis reagent additionally comprises magnetic particles as the component associated with the material of interest.

18. The method of claim 15, wherein the one or more chambers preceding the first chamber comprise a chamber filled with a lysis reagent and a chamber filled with a wash medium.

19. The method of claim 18, wherein the second chamber comprises a reagent selected from the group consisting of an elution medium, an amplification reagent, or both.

20. The method of claim 1, wherein the sample comprising a material of interest is a biological sample that has been processed prior to placing in the first chamber of the device.

21. The method of claim 1, wherein the sample comprising a material of interest that is placed in the first chamber is a biological sample that has been processed in a chamber of the device that precedes the first chamber.

* * * * *